(12) United States Patent
Dimanche-Boitrel et al.

(10) Patent No.: US 10,457,678 B2
(45) Date of Patent: Oct. 29, 2019

(54) SUBSTITUTED PYRROLO[2,3-B]PYRIDINES AS INHIBITORS OF CELLULAR NECROPTOSIS

(71) Applicants: Institut National de la Sante et de la Recherche Medicale (INSERM), Paris (FR); Centre National de la Recherche Scientifique (CNRS), Paris (FR); Sorbonne Universite, Paris (FR); Universite Claude Bernard Lyon 1, Villeurbanne (FR)

(72) Inventors: Marie-Thérèse Dimanche-Boitrel, Melesse (FR); Stéphane Bach, Sibiril (FR); Claire Delehouze, La Roche Maurice (FR); Peter Goekjian, Villeurbanne (FR); Arnaud Comte, Lyons (FR)

(73) Assignees: Institut National de la Sante et de la Recherche Medicale (INSERM), Paris (FR); Centre National de la Recherche Scientifique (CNRS), Paris (FR); Sorbonne Universite, Paris (FR); Universite Claude Bernard Lyon 1, Villeurbanne (FR)

( * ) Notice: Subject to any disclaimer, the term of this patent is extended or adjusted under 35 U.S.C. 154(b) by 0 days.

(21) Appl. No.: 15/768,395

(22) PCT Filed: Oct. 13, 2016

(86) PCT No.: PCT/EP2016/074637
§ 371 (c)(1),
(2) Date: Apr. 13, 2018

(87) PCT Pub. No.: WO2017/064216
PCT Pub. Date: Apr. 20, 2017

(65) Prior Publication Data
US 2018/0312502 A1  Nov. 1, 2018

(30) Foreign Application Priority Data
Oct. 13, 2015  (EP) .................................... 15306623

(51) Int. Cl.
*A61K 31/437* (2006.01)
*C07D 471/04* (2006.01)
(52) U.S. Cl.
CPC .................. *C07D 471/04* (2013.01)
(58) Field of Classification Search
CPC ......................... A61K 31/437; C07D 471/04
USPC ......................................... 514/300; 546/113
See application file for complete search history.

(56) References Cited

U.S. PATENT DOCUMENTS 8,143,300 B2   3/2012   Cuny et al.

FOREIGN PATENT DOCUMENTS

WO    9847899 A1    10/1998
WO    2011090738 A2   7/2011
WO    2012125544 A2   9/2012

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Rossy, et al. Beilstein Journal of Organic Chemistry, 9, 2013, 1426-1431.*
Makida, et al. Angewandte Chemie, International Edition, 55(39), 2016, 11859-11862.*
Miao, Benchun, and Alexei Degterev. "Methods to analyze cellular necroptosis." Apoptosis. Humana Press, Totowa, NJ, 2009, Chapter 6, pp. 79-93.
Linkermann A, Green DR. Necroptosis. New England Journal of Medicine. Jan. 30, 2014;370(5):455-465.
Jouan-Lanhouet S, Riquet F, Duprez L, Berghe TV, Takahashi N, Vandenabeele P. Necroptosis, in vivo detection in experimental disease models. Seminars in cell & developmental biology Nov. 1, 2014 (vol. 35, pp. 2-13). Academic Press http://dx.doi.org/10.1016/j.semcdb.2014.08.010.
Strilic B, Yang L., Albarrán-Juárez J, Wachsmuth L, Han K, Müller UC, Pasparakis M, Offermanns S. Tumour-cell-induced endothelial cell necroptosis via death receptor 6 promotes metastasis. Nature. Aug. 2016;536(7615):215.
Degterev A, Huang Z, Boyce M, Li Y, Jagtap P, Mizushima N, Cuny GD, Mitchison TJ, Moskowitz MA, Yuan J. Chemical inhibitor of nonapoptotic cell death with therapeutic potential for ischemic brain injury. Nature chemical biology. Jul. 2005;1(2):112.
Degterev A, Hitomi J, Germscheid M, Ch'en IL, Korkina O, Teng X, Abbott D, Cuny GD, Yuan C, Wagner G, Hedrick SM. Identification of RIP1 kinase as a specific cellular target of necrostatins. Nature chemical biology. May 2008;4 (5):313.
Cho Y, McQuade T, Zhang H, Zhang J, Chan FK. RIP1-dependent and independent effects of necrostatin-1 in necrosis and T cell activation. PloS one. Aug. 10, 2011;6(8):e23209.

(Continued)

*Primary Examiner* — Douglas M Willis
(74) *Attorney, Agent, or Firm* — Lerner, David, Littenberg, Krumholz & Mentlik, LLP

(57) ABSTRACT

The present invention relates to new N1- and N7-substituted sibiriline derivatives of the following general formula (I): (I) or a pharmaceutically acceptable salt and/or solvate thereof, notably for use as drug, in particular for use as inhibitor of cellular necroptosis. The present invention also relates to a pharmaceutical composition comprising such a compound and processes to prepare such a compound. The present invention also encompasses the use of a compound of the general formula (I) for organs preservation.

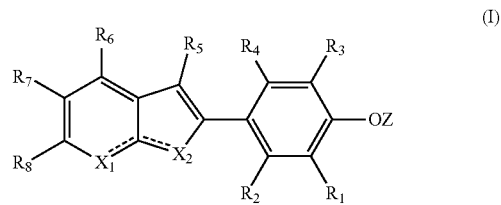

(I)

19 Claims, 6 Drawing Sheets

(56) References Cited

OTHER PUBLICATIONS

Takahashi N, Duprez L., Grootjans S, Cauwels A, Nerinckx W, DuHadaway JB, Goossens V, Roelandt R, Van Hauwermeiren F, Libert C, Declercq W. Necrostatin-1 analogues: critical issues on the specificity, activity and in vivo use in experimental disease models. Cell death & disease. Nov. 2012;3(11):e437.

Jagtap PG, Degterev A, Choi S, Keys H, Yuan J, Cuny GD. Structure-activity relationship study of tricyclic necroptosis inhibitors. Journal of medicinal chemistry. Apr. 19, 2007;50(8):1886-1895.

Teng X, Keys H, Jeevanandam A, Porco Jr JA, Degterev A, Yuan J, Cuny GD. Structure-activity relationship study of [1, 2, 3] thiadiazole necroptosis inhibitors. Bioorganic & medicinal chemistry letters. Dec. 15, 2007;17(24):6836-6840.

Wang K, Li J, Degterev A, Hsu E, Yuan J, Yuan C. Structure-activity relationship analysis of a novel necroptosis inhibitor, Necrostatin-5. Bioorganic & medicinal chemistry letters. Mar. 1, 2007;17(5):1455-1465.

Zheng W, Degterev A, Hsu E, Yuan J, Yuan C. Structure-activity relationship study of a novel necroptosis inhibitor, necrostatin-7. Bioorganic & medicinal chemistry letters. Sep. 15, 2008;18(18):4932-4935.

Wu Z, Li Y, Cai Y, Yuan J, Yuan C. A novel necroptosis inhibitor—necrostatin-21 and its SAR study. Bioorganic & medicinal chemistry letters. Sep. 1, 2013;23(17):4903-4906.

Xie T, Peng W, Liu Y, Yan C, Maki J, Degterev A, Yuan J, Shi Y. Structural basis of RIP1 inhibition by necrostatins. Structure. Mar. 5, 2013;21(3):493-499.

Khalid Mohammed et al.: 11 Synthesis of new pyrrolo[2.3-b]pyridines as a potent inhibitor of tumor necrosis factor alpha—. Arch. Pharm. Pharm. Med. Chem ., vol. 337, Jul. 4, 2003 (Jul. 4, 2003). pp. 15-19. XP002755677.

International Search Report for PCT/EP2016/074637 (published as WO2017064216) dated Jan. 18, 2017.

\* cited by examiner

SUBSTITUTED PYRROLO[2,3-B]PYRIDINES AS INHIBITORS OF CELLULAR NECROPTOSIS

CROSS REFERENCE TO RELATED APPLICATIONS

The present application is a national phase entry under 35 U.S.C. § 371 of International Application No. PCT/EP2016/074637, filed Oct. 13, 2016, which claims priority from European Patent Application No. 15306623.8 filed Oct. 13, 2015, all of which are hereby incorporated herein by reference.

The present invention relates to new N1- and N7-substituted sibiriline derivatives as well as their preparation processes and their use as inhibitor of cellular necroptosis. The present invention also relates to a pharmaceutical composition comprising said N1- and N7-substituted sibiriline derivatives and their use for inhibiting cellular necroptosis, in particular for preventing and/or treating disorders associated with cellular necroptosis.

Programmed cell death is a natural process for removing unwanted cells, such as cancer cells. Necroptosis is clearly distinct from apoptosis as it does not involve key apoptosis regulators, such as caspases, Bcl-2 family members or cytochrome c release from mitochondria. "Necroptosis" is a specialized biochemical pathway of programmed necrosis that depends notably on the serine/threonine kinase activity of RIPK1 (Receptor-Interacting Protein Kinase 1). It can be inhibited by necrostatin-1, an inhibitor of RIPK1 (U.S. Pat. No. 8,143,300).

Necroptosis may be activated upon stimulation by TNF-α (Tumor Necrosis Factor α), FasL (Fas ligand) and TRAIL (Tumor-necrosis-factor Related Apoptosis Inducing Ligand), and relies on the activity of two serine-threonine kinases, RIPK1 and RIPK3. TNF via TNFR1 (Tumor Necrosis Factor Receptor 1) leads to the formation of two sequential signaling complexes. The receptor-proximal complex I induces pro-survival signals through activation of NF-κB (Nuclear Factor—kappa B) and MAPKs (Mitogen Activated Protein Kinases), while the second cytosolic complex II signals two cell death pathways: (a) apoptosis via formation of complex IIa including FADD (Fas-Associated Death Domain) that recruits caspase-8 and/or caspase-10 to activate a caspase cascade; (b) necroptosis via activation of RIPK1 and RIPK3 kinases in a complex called the necrosome. TNF-α can induce necrosis in Jurkat cells when FADD is deleted (Miao and Degterev, *Methods Mol. Biol.* 2009, 559, 79-93).

The ground-breaking finding that necroptosis is a genetically controlled process led to the hypothesis that this programmed cell-death is 'druggable', an emerging breakthrough that carries the potential to revolutionize every day clinical medicine (Linkermann and Green, *N. Eng. J. Med.* 2014, 370(5), 455-465). Indeed molecular targets, including RIPK1, RIPK3 and MLKL (Mixed Lineage Kinase domain-Like), have convincingly been shown to contribute to multiple disorders where necroptosis is of central pathophysiological relevance, such as: ischemia-reperfusion injury in brain, heart and kidney, inflammatory diseases, sepsis, retinal disorders, neurodegenerative diseases and infectious disorders (Jouan-Lanhouet et al. *Semin. Cell. Dev. Biol.* 2014, 35, 2-13). More recently, it has been shown that human and murine tumour cells induce necroptosis of endothelial cells, which promotes tumour cell extravasation and metastasis (Strilic et al. *Nature* 2016, 536(7615), 215-218). Necroptosis can thus also be targeted in the treatment of human metastasis, the leading cause of cancer-related death in humans.

Only few RIPK1 inhibitors have been developed (Degterev et al. *Nat. Chem. Biol.* 2005, 1(2), 112-119, and *Nat Chem Biol.* 2008, 4(5), 313-321). Among them, necrostatin-1 (Nec-1) has been used to specifically inhibit several necrotic processes. However, RIPK1-independent effect of Nec-1 has been pointed out (Cho et al. *PLoS One.* 2011, 6(8):e23209), and Nec-1 is also an inhibitor of indoleamine 2, 3-dioxygenase (Takahashi et al. *Cell Death Dis.* 2012, 3:e437). Moreover, the stability of Nec-1 in vivo is very limited. Several structurally distinct necrostatins (Nec-3 (Jagtap et al. *J. Med. Chem.* 2007, 50(8), 1886-1895), Nec-4 (Teng et al. *Bioorg. Med. Chem. Lett.* 2007, 17(24), 6836-6840), Nec-5 (Wang et al. *Bioorg. Med. Chem. Lett.* 2007, 17(5), 1455-1465), Nec-7 (Zheng et al. *Bioorg. Med. Chem. Lett.* 2008, 18(18), 4932-4935)) and corresponding modifications have been reported. Recently, Nec-21, another potent Nec-1 analogue was reported to show an improved off-target profile (Wu et al. *Bioorg. Med. Chem. Lett.* 2013, 23(17), 4903-4906). One of the best stable RIPK1 inhibitor is Nec-1s (Nec-1 stable), which was shown to interact with a hydrophobic pocket of the kinase domain, hence stabilizing RIPK1 in an inactive conformation (Xie et al. *Structure* 2013, 21(3), 493-9).

There is therefore a need for new RIPK1 inhibitors with high potency, good stability and low toxicity.

The inventors of the present invention have thus discovered new sibiriline derivatives (N1- and N7-substituted sibiriline derivatives) that inhibit the necroptotic cell-death. These compounds thus appear to be very attractive in therapy for preventing and/or treating disorders associated with cellular necroptosis. Besides, such compounds can also be used for the preservation and/or protection of biological materials such as cells, tissues, body fluids and organs, and of microorganisms, advantageously as a medical device.

Thus, the present invention relates to a compound of the following general formula (I):

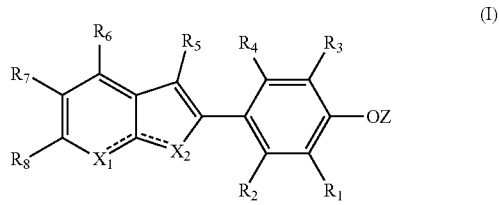

or a pharmaceutically acceptable salt and/or solvate thereof, wherein:

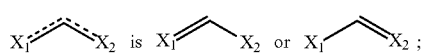

when

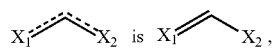

$X_1$ is a nitrogen atom and —$X_2$ is —N—Y, when

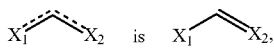

—$X_1$ is —N—Y and $X_2$ is a nitrogen atom,

Y is —$OR_9$; —$C(O)NR_{10}R_{11}$; —$C(O)R_{12}$; —$R_{13}C(O)OR_{14}$; —$R_{15}C(O)R_{16}$; —$R_{17}NR_{18}R_{19}$; —$R_{20}OR_{21}$; —$R_{22}OR_{23}Si(R_{24})_3$; —$S(O)_2R_{25}$; —$OR_{26}C(O)OR_{27}$; —$OC(O)R_{28}$; —$C(O)OR_{29}$; O—$SO_2$—$NR_{30}R_{31}$; —$SO_2$—$NR_{30}R_{31}$; or a group selected from $(C_1$-$C_6)$alkyl, heterocycloalkyl, aryl, heteroaryl, —$(C_1$-$C_6)$alkyl-aryl, and —$(C_1$-$C_6)$alkyl-heterocycloalkyl, said group being optionally substituted with one or several groups selected from halo, heterocycle, —$OR_{32}$, —$NR_{33}R_{34}$, —$SR_{35}$, —$S(O)R_{36}$, —$SO_2R_{37}$, —$SO_2NR_{38}R_{39}$, —$OCOR_{40}$, —$NR_{41}COR_{42}$, —$NR_{43}C(O)OR_{44}$, —$CO_2R_{45}$, —$CONR_{46}R_{47}$, —$CO_2R_{48}$, —$OCONR_{49}R_{50}$, —$COR_{40}$, nitro (—$NO_2$), cyano (—CN) and oxo (=O);

Z is H or a $(C_1$-$C_6)$alkyl and $R_1$ is H, halo, $(C_1$-$C_6)$alkyl, —$OR_{51}$, $CF_3$, —$NR_{52}R_{53}$, —$OS(O)_2NR_{54}R_{55}$ or —CN; or Z and $R_1$ together form a heterocycloalkyl;

$R_2$ to $R_4$ are, independently of one another, H, halo, $(C_1$-$C_6)$alkyl, —$OR_{51}$, $CF_3$, —$NR_{52}R_{53}$, —$OS(O)_2NR_{54}R_{55}$ or —CN;

$R_5$ is H or $(C_1$-$C_6)$alkyl; and $R_6$ to $R_8$ are, independently of one another, H, halo, —$OR_{56}$, —$NR_{57}R_{58}$, —$C(O)NR_{59}R_{60}$; —$C(O)R_{61}$; —$R_{62}C(O)OR_{63}$; —$R_{64}C(O)R_{65}$; —$R_{66}NR_{67}R_{68}$; —$R_{69}OR_{70}$; —$R_{71}OR_{72}Si(R_{73})_3$; —$S(O)_2R_{74}$; —$OR_{75}C(O)OR_{76}$; —$OC(O)R_{77}$; —$C(O)OR_{78}$; or a group selected from $(C_1$-$C_6)$alkyl, heterocycloalkyl, aryl, heteroaryl, —$(C_1$-$C_6)$alkyl-aryl, —$(C_1$-$C_6)$alkyl-heterocycloalkyl, said group being optionally substituted with one or several groups selected from halo, —$OR_{79}$, —$NR_{80}R_{81}$, —$SR_{82}$, —$S(O)R_{83}$, —$SO_2R_{84}$, —$SO_2NR_{85}R_{86}$, —$OCOR_{87}$, —$NR_{88}COR_{89}$, —$NR_{90}C(O)OR_{91}$, —$CO_2R_{92}$, —$CONR_{93}R_{94}$, —$CO_2R_{95}$, —$OCONR_{96}R_{97}$, —$COR_{98}$, nitro (—$NO_2$), cyano (—CN), oxo (=O); and $R_9$ to $R_{98}$ are, independently of one another, H, halo, or a group selected from $(C_1$-$C_6)$alkyl, aryl, heteroaryl, heterocycloalkyl, —$(C_1$-$C_6)$alkyl-aryl; or $R_{18}$-$R_{19}$, $R_{33}$-$R_{34}$, $R_{46}$-$R_{47}$, $R_{49}$-$R_{50}$, $R_{57}$-$R_{58}$, $R_{59}$-$R_{60}$, $R_{67}$-$R_{68}$, $R_{80}$-$R_{81}$, $R_{85}$-$R_{86}$, $R_{93}$-$R_{94}$, and/or $R_{96}$-$R_{97}$ respectively form together a heterocycloalkyl group.

proviso that: when

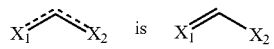

and Z is a methyl, Y is not a group selected from methyl or —$SO_2$-phenyl.

In a preferred embodiment:

Y is —$C(O)NR_{10}R_{11}$; —$C(O)R_{12}$; —$S(O)_2R_{25}$; —$C(O)OR_{29}$ or —$SO_2$—$NR_{30}R_{31}$;

Z is a $(C_1$-$C_6)$alkyl and $R_1$ is H, halo, $(C_1$-$C_6)$alkyl, —$OR_{51}$, $CF_3$, —$NR_{52}R_{53}$, —$OS(O)_2NR_{54}R_{55}$ or —CN; or Z and $R_1$ together form a heterocycloalkyl;

$R_2$ to $R_4$ are, independently of one another, H, halo, $(C_1$-$C_6)$alkyl, —$OR_{51}$, —$CF_3$, —$NR_{52}R_{53}$, —$OS(O)_2NR_{54}R_{55}$ or —CN;

$R_5$ is H, $(C_1$-$C_6)$alkyl or —O—$(C_1$-$C_6)$alkyl;

$R_6$ to $R_8$ are, independently of one another, H; halo; —$OR_{56}$; —$NR_{57}R_{58}$; —$C(O)NR_{59}R_{60}$; —$C(O)R_{61}$; —$R_{62}C(O)OR_{63}$; —$R_{64}C(O)R_{65}$; —$R_{66}NR_{67}R_{68}$; —$R_{69}OR_{70}$; —$S(O)_2R_{74}$; —$OR_{75}C(O)OR_{76}$; —$OC(O)R_{77}$; —$C(O)OR_{78}$; or a group selected from $(C_1$-$C_6)$alkyl, heterocycloalkyl, aryl, heteroaryl, —$(C_1$-$C_6)$alkyl-aryl, —$(C_1$-$C_6)$alkyl-heterocycloalkyl, said group being optionally substituted with one or several groups selected from halo, —$OR_{79}$, —$NR_{80}R_{81}$, —$SR_{82}$, —$S(O)R_{83}$, —$SO_2R_{84}$, —$SO_2NR_{85}R_{86}$, —$OCOR_{87}$, —$NR_{88}COR_{89}$, —$NR_{90}C(O)OR_{91}$, —$CO_2R_{92}$, —$CONR_{93}R_{94}$, —$CO_2R_{95}$, —$OCONR_{96}R_{97}$, —$COR_{98}$, nitro (—$NO_2$), cyano (—CN) and oxo (=O); and $R_{10}$ to $R_{12}$, $R_{25}$, $R_{29}$ to $R_{31}$ and $R_{51}$ to $R_{98}$ are, independently of one another, H; halo; or a group selected from $(C_1$-$C_6)$alkyl, aryl, heteroaryl, heterocycloalkyl and —$(C_1$-$C_6)$alkyl-aryl, said group being optionally substituted with one or several groups selected from halo, $(C_1$-$C_6)$alkyl, —$C(O)R_{alk}$, —$C(O)OR_{alk}$, —$SO_2R_{alk}$, —$OR_{alk}$, —$COR_{alk}R_{alk}'$, oxo (=O), and $SO_2$-$R_{alk}$, wherein $R_{alk}$ and $R_{alk}'$ are, independently of each other, $(C_1$-$C_6)$alkyl;

or $R_{57}$-$R_{58}$, $R_{59}$-$R_{60}$, $R_{67}$-$R_{68}$, $R_{80}$-$R_{81}$, $R_{85}$-$R_{86}$, $R_{93}$-$R_{94}$, and/or $R_{96}$-$R_{97}$ respectively form together a heterocycloalkyl group;

with the proviso that: when

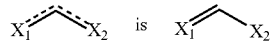

and Z is a methyl, Y is not —$SO_2$-phenyl.

For the purpose of the invention, the term "pharmaceutically acceptable" is intended to mean what is useful to the preparation of a pharmaceutical composition, and what is generally safe and non-toxic, for a pharmaceutical use.

The term "pharmaceutically acceptable salt or solvate" is intended to mean, in the framework of the present invention, a salt or solvate of a compound which is pharmaceutically acceptable, as defined above, and which possesses the pharmacological activity of the corresponding compound.

The pharmaceutically acceptable salts comprise:

(1) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic, and trifluoroacetic acid and the like, and (2) base addition salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

Acceptable solvates for the therapeutic use of the compounds of the present invention include conventional solvates such as those formed during the last step of the preparation of the compounds of the invention due to the presence of solvents. As an example, mention may be made of solvates due to the presence of water (these solvates are also called hydrates) or ethanol.

The terms "$(C_1-C_6)$alkyl", as used in the present invention, refers to a straight or branched saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The term "aryl", as used in the present invention, refers to an aromatic hydrocarbon group comprising preferably 6 to 10 carbon atoms and comprising one or more, notably 1 or 2, fused rings, such as, for example, a phenyl or naphtyl group, advantageously a phenyl group.

The term "—$(C_1-C_6)$alkyl-aryl", as used in the present invention, refers to an aryl group as defined above bound to the molecule via a $(C_1-C_6)$alkyl group as defined above. In particular, the —$(C_1-C_6)$alkyl-aryl group is a benzyl group.

The term "heterocycle" as used in the present invention refers to a saturated, unsaturated or aromatic hydrocarbon monocycle or polycycle (comprising fused, bridged or spiro rings), such as a bicycle, in which one or more, advantageously 1 to 4, and more advantageously 1 or 2, carbon atoms have each been replaced with a heteroatom selected from nitrogen, oxygen and sulphur atoms, and notably being a nitrogen atom. Advantageously, the heterocycle comprises 5 to 15, notably 5 to 10 atoms in the ring(s). Each ring of the heterocycle has advantageously 5 or 6 members.

According to a particular embodiment, the heterocycle is a saturated, unsaturated or aromatic hydrocarbon monocycle or bicycle (comprising fused, bridged or spiro rings, notably fused rings), each cycle having 5 or 6 members and 1 to 4, notably 1 or 2, carbon atoms having each been replaced with a nitrogen or oxygen atom, notably a nitrogen atom.

A heterocycle can be notably thiophene, furan, dioxane, dioxalane, pyrrole, imidazole, pyrazole, oxazole, isoxazole, thiazole, isothiazole, triazoles (1,2,3-triazole and 1,2,4-triazole), benzofuran, tetrahydrofuran, indole, benzothiophene, benzimidazole, indazole, benzoxazole, benzisoxazole, benzothiazole, benzisothiazole, pyridine, pyrimidine, pyridazine, pyrazine, triazine, quinoline, isoquinoline, quinoxaline, quinazoline, piperidine, piperazine, triazinane, morpholine, pyrrolidine, imidazolidine, dihydropyridines, dihydropyrimidines (notably 1,2-dihydropyrimidine), dihydropyridazines, dihydropyrazines, dihydrotriazines, tetrahydropyridines, tetrahydropyrimidines, tetrahydropyridazines, tetrahydropyrazines, tetrahydrotriazines, etc.

The term "—$(C_1-C_6)$alkyl-heterocycle" as used in the present invention refers to a heterocycle group as defined above bound to the molecule via a $(C_1-C_6)$alkyl group as defined above. In particular, the —$(C_1-C_6)$alkyl-heterocycle group is a methylmorpholinyl or methylpiperazinyl group.

The term "heterocycloalkyl" as used in the present invention refers to a saturated heterocycle as defined above.

According to a particular embodiment of the present invention, the term "heterocycloalkyl" refers to a saturated hydrocarbon ring having 5 to 7 members, in which one or more, advantageously one or two, carbon atoms have been each replaced with a heteroatom, such as sulphur, nitrogen or oxygen atoms. It can be notably a 1,3-dioxolanyl, 1,4-dioxanyl, tetrahydrofuranyl, piperidinyl, piperazinyl, pyrrolidinyl, imidazolidinyl or tetrahydropyranyl group.

The term "heteroaryl" as used in the present invention refers to an aromatic heterocycle as defined above.

According to a particular embodiment, the heteroaryl is an aromatic hydrocarbon monocycle or bicycle (i.e. comprising two fused rings), each cycle having 5 or 6 members, notably 6 members, and 1 to 4, notably 1 or 2, carbon atoms having each been replaced with a nitrogen or oxygen atom, notably a nitrogen atom.

A heteroaryl can be notably thiophene, furan, pyrrole, imidazole, pyrazole, oxazole, isoxazole, thiazole, isothiazole, triazoles (1,2,3-triazole and 1,2,4-triazole), benzofuran, indole, benzothiophene, benzimidazole, indazole, benzoxazole, benzisoxazole, benzothiazole, benzisothiazole, pyridine, pyrimidine, pyridazine, pyrazine, triazine, quinoline, isoquinoline, quinoxaline, quinazoline, etc. In particular, the heteroaryl is thiophene, imidazole, benzimidazole, pyrazine or isoquinoline.

The term "halogen", as used in the present invention, refers to a fluorine, bromine, chlorine or iodine atom.

According to a particular embodiment of the present invention, Z is $(C_1-C_3)$alkyl, preferably ethyl.

Z can also form together with $R_1$ a heterocycloalkyl, preferably a 1,3-dioxolanyl or 1,4-dioxanyl group.

In the above definitions of Z, the $(C_1-C_6)$alkyl is preferably methyl, ethyl or isopropyl, more preferably ethyl.

When Z is $(C_1-C_6)$alkyl, $R_1$ is H, halo, $(C_1-C_6)$alkyl, —$OR_{51}$, $CF_3$, —$NR_{52}R_{53}$, —$OS(O)_2NR_{54}R_{55}$ or —CN, in particular H, halo, $(C_1-C_6)$alkyl or —$OR_{51}$, preferably H, halo, methyl or OMe, more preferably H; $R_{51}$ to $R_{55}$ being as defined above.

In a preferred embodiment, $R_2$ to $R_4$ represents, independently of one another, H, halo, $(C_1-C_6)$alkyl or —$OR_{51}$, preferably H, halo, methyl or OMe, more preferably H.

In a preferred embodiment, $R_5$ is H or $(C_1-C_6)$alkyl, more preferably H.

In a preferred embodiment, $R_6$ to $R_8$ are, independently of one another, H; halo; —$OR_{56}$; —$NR_{57}R_{58}$; or a group selected from $(C_1-C_6)$alkyl, heterocycloalkyl, aryl, heteroaryl, —$(C_1-C_6)$alkyl-aryl and —$(C_1-C_6)$alkyl-heterocycloalkyl, said group being optionally substituted with one or several groups selected from halo, —$OR_{79}$, —$NR_{80}R_{81}$, —$SR_{82}$, —$S(O)R_{83}$, —$SO_2R_{84}$, —$SO_2NR_{85}R_{86}$, —$OCOR_{87}$, —$NR_{88}COR_{89}$, —$NR_{90}C(O)OR_{91}$, —$CO_2R_{92}$, —$CONR_{93}R_{94}$, —$CO_2R_{95}$, —$OCONR_{96}R_{97}$, —$COR_{98}$, nitro (—$NO_2$), cyano (—CN), oxo (=O); preferably H, halo, —$OR_{56}$, —$NR_{57}R_{58}$; or a group selected from $(C_1-C_6)$alkyl, heterocycloalkyl, aryl and heteroaryl; $R_{56}$ to $R_{98}$ being as defined above.

In particular, $R_6$ to $R_8$ are, independently of one another, H; halo; —$OR_{56}$; —$NR_{57}R_{58}$; or a group selected from $(C_1-C_6)$alkyl, heterocycloalkyl, aryl, heteroaryl, —$(C_1-C_6)$alkyl-aryl and —$(C_1-C_6)$alkyl-heterocycloalkyl, said group being optionally substituted with one or several groups selected from halo, —$OR_{79}$; $R_{56}$ to $R_{58}$ and $R_{79}$ being as defined above.

In particular, $R_6$ to $R_8$ are, independently of one another, H, halo, —$OR_{56}$, —$NR_{57}R_{58}$; $R_{56}$ to $R_{58}$ being as defined above.

More particularly, $R_6$ to $R_8$ are, independently of one another, H or halo.

In a particular embodiment of the present invention,

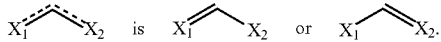

When

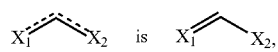

$X_1$ is a nitrogen atom and —$X_2$ is —N—Y, the compound obtained is thus N1-substituted, whereas when

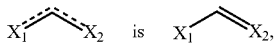

—$X_1$ is —N—Y and $X_2$ is a nitrogen atom, the compound obtained is thus N7-substituted.

In the above definitions of

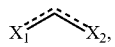

—Y is —$OR_9$; —$C(O)NR_{10}R_{11}$; —$C(O)R_{12}$; —$R_{13}C(O)OR_{14}$; —$R_{15}C(O)R_{16}$; —$R_{17}NR_{18}R_{19}$; —$R_{20}OR_{21}$; —$R_{22}OR_{23}Si(R_{24})_3$; —$S(O)_2R_{25}$; —$OR_{26}C(O)OR_{27}$; —$OC(O)R_{28}$; —$C(O)OR_{29}$; —O—$SO_2$—$NR_{30}R_{31}$; or a group selected from ($C_1$-$C_6$)alkyl, heterocycloalkyl, aryl, heteroaryl, —($C_1$-$C_6$)alkyl-aryl, and —($C_1$-$C_6$)alkyl-heterocycloalkyl, said group being optionally substituted with one or several groups selected from halo, heterocyle, —$OR_{32}$, —$NR_{33}R_{34}$, —$SR_{35}$, —$S(O)R_{36}$, —$SO_2R_{37}$, —$SO_2NR_{38}R_{39}$, —$OCOR_{40}$, —$NR_{41}COR_{42}$, —$NR_{43}C(O)OR_{44}$, —$CO_2R_{45}$, —$CONR_{46}R_{47}$, —$CO_2R_{48}$, —$OCONR_{49}R_{50}$, —COR, nitro (—$NO_2$), cyano (—CN) and oxo (═O); $R_9$ to $R_{50}$ being as defined above.

In particular, Y is —$OR_9$; —$C(O)NR_{10}R_{11}$; —$C(O)R_{12}$; —$R_{13}C(O)OR_{14}$; —$R_{15}C(O)R_{16}$; —$R_{17}NR_{18}R_{19}$; —$R_{20}OR_{21}$; —$R_{22}OR_{23}Si(R_{24})_3$; —$S(O)_2R_{25}$; —$OR_{26}C(O)OR_{27}$; —$OC(O)R_{28}$; —$C(O)OR_{29}$; or a group selected from ($C_1$-$C_6$)alkyl, heterocycloalkyl, aryl, heteroaryl, —($C_1$-$C_6$)alkyl-aryl, and —($C_1$-$C_6$)alkyl-heterocycloalkyl, said group being optionally substituted with one or several groups selected from halo, heterocyle, —$OR_{32}$ and —$NR_{33}R_{34}$; $R_9$ to $R_{34}$ being as defined above.

In particular, Y is —$OR_9$; —$C(O)NR_{10}R_{11}$; —$C(O)R_{12}$; —$R_{13}C(O)OR_{14}$; —$R_{15}C(O)R_{16}$; —$R_{17}NR_{18}R_{19}$; —$R_{20}OR_{21}$; —$R_{22}OR_{23}Si(R_{24})_3$; —$S(O)_2R_{25}$; —$OR_{26}C(O)OR_{27}$; —$OC(O)R_{28}$; —$C(O)OR_{29}$; or a group selected from ($C_1$-$C_6$)alkyl, heterocycloalkyl, aryl, heteroaryl, —($C_1$-$C_6$)alkyl-aryl, and —($C_1$-$C_6$)alkyl-heterocycloalkyl, said group being optionally substituted with one or several groups selected from halo, heterocycle or —$OR_{32}$; $R_9$ to $R_{32}$ being as defined above.

In a preferred embodiment, Y is —$C(O)NR_{10}R_{11}$; —$C(O)R_{12}$; —$S(O)_2R_{25}$; —$C(O)OR_{29}$ or —$SO_2$—$NR_{30}R_{31}$.

In all the above definitions, $R_9$ to $R_{98}$ are, independently of one another, H, halo, or a group selected from ($C_1$-$C_6$) alkyl, aryl, heteroaryl, heterocycloalkyl, —($C_1$-$C_6$)alkyl-aryl; or $R_{18}$-$R_{19}$, $R_{33}$-$R_{34}$, $R_{46}$-$R_{47}$, $R_{49}$-$R_{50}$, $R_{57}$-$R_{58}$, $R_{59}$-$R_{60}$, $R_{67}$-$R_{68}$, $R_{80}$-$R_{81}$, $R_{85}$-$R_{86}$, $R_{93}$-$R_{94}$, and/or $R_{96}$-$R_{97}$ respectively form together a heterocycloalkyl group.

In particular, $R_9$ to $R_{98}$ are, independently of one another, preferably H, halo, or a group selected from ($C_1$-$C_6$)alkyl, phenyl, benzyl, thiophenyl, pyridinyl, pyrrolidinyl and morpholinyl.

In a preferred embodiment, $R_{10}$ to $R_{12}$, $R_{25}$, $R_{29}$ to $R_{31}$ and $R_{51}$ to $R_{98}$ are, independently of one another, H; halo; or a group selected from ($C_1$-$C_6$)alkyl, aryl, heteroaryl, heterocycloalkyl and —($C_1$-$C_6$)alkyl-aryl, said group being optionally substituted with one or several groups selected from halo, ($C_1$-$C_6$)alkyl, —$C(O)R_{alk}$, —$C(O)OR_{alk}$, —$SO_2R_{alk}$, —$OR_{alk}$, —$COR_{alk}R_{alk}'$, oxo (═O), and $SO_2$-$R_{alk}$, wherein $R_{alk}$ and $R_{alk}'$ are, independently of each other, ($C_1$-$C_6$)alkyl;

or $R_{57}$-$R_{58}$, $R_{59}$-$R_{60}$, $R_{67}$-$R_{68}$, $R_{80}$-$R_{81}$, $R_{85}$-$R_{86}$, $R_{93}$-$R_{94}$, and/or $R_{96}$-$R_{97}$ respectively form together a heterocycloalkyl group;

More particularly, $R_{10}$ to $R_{12}$, $R_{25}$, $R_{29}$ to $R_{31}$ and $R_{51}$ to $R_{98}$ are, independently of one another, H; halo; or a group selected from ($C_1$-$C_6$)alkyl, phenyl, benzyl, heterocycloalkyl, said group being optionally substituted with one or several groups selected from halo, ($C_1$-$C_6$)alkyl, —$C(O)R_{alk}$, —$C(O)OR_{alk}$, —$SO_2R_{alk}$, —$OR_{alk}$, —$COR_{alk}R_{alk}'$, oxo (═O), and $SO_2$-$R_{alk}$, wherein $R_{alk}$ and $R_{alk}'$ are, independently of each other, ($C_1$-$C_6$)alkyl, preferably selected from halo, methyl, oxo (═O), and $SO_2$—$CH_3$.

In a particular embodiment, $R_{10}$ to $R_{11}$, $R_{25}$, $R_{30}$ to $R_{31}$ and $R_{51}$ to $R_{98}$ are, independently of one another, H; halo; or a group selected from ($C_1$-$C_6$)alkyl, aryl, heteroaryl, heterocycloalkyl and —($C_1$-$C_6$)alkyl-aryl.

In another particular embodiment, $R_{12}$ and $R_{29}$ are, independently of one another, H; halo; or a group selected from ($C_1$-$C_6$)alkyl, aryl, heteroaryl, heterocycloalkyl and —($C_1$-$C_6$)alkyl-aryl, said group being optionally substituted with one or several groups selected from halo, ($C_1$-$C_6$)alkyl, —$C(O)R_{alk}$, —$C(O)OR_{alk}$, —$SO_2R_{alk}$, —$OR_{alk}$, —$COR_{alk}R_{alk}'$, oxo (═O), and $SO_2$-$R_{alk}$, wherein $R_{alk}$ and $R_{alk}'$ are, independently of each other, ($C_1$-$C_6$)alkyl, preferably selected from halo, methyl, oxo (═O), and $SO_2$—$CH_3$.

More particularly, $R_{12}$ is H; halo; or a group selected from ($C_1$-$C_6$)alkyl, heterocycloalkyl and —($C_1$-$C_6$)alkyl-aryl, said group being optionally substituted with one or several groups selected from halo, ($C_1$-$C_6$)alkyl, —$C(O)R_{alk}$, —$C(O)OR_{alk}$, —$SO_2R_{alk}$, —$OR_{alk}$, —$COR_{alk}R_{alk}'$, oxo (═O), and $SO_2$-$R_{alk}$, wherein $R_{alk}$ and $R_{alk}'$ are, independently of each other, ($C_1$-$C_6$)alkyl, preferably selected from halo, methyl, oxo (═O), and $SO_2$—$CH_3$.

According to a particular embodiment of the present invention, in the following general formula (I) or a pharmaceutically acceptable salt and/or solvate thereof:

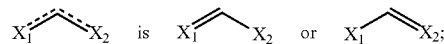

when

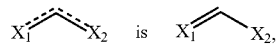

$X_1$ is a nitrogen atom and —$X_2$ is —N—Y, when

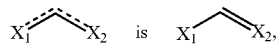

—$X_1$ is —N—Y and $X_2$ is a nitrogen atom,
Y is —$OR_9$, —$C(O)NR_{10}R_{11}$; —$C(O)R_{12}$; —$R_{13}C(O)OR_{14}$; —$R_{15}C(O)R_{16}$; —$R_{17}NR_{18}R_{19}$; —$R_{20}OR_{21}$; —$R_{22}OR_{23}Si(R_{24})_3$; —$S(O)_2R_{25}$; —$OR_{26}C(O)OR_{27}$; —$OC(O)R_{28}$; —$C(O)OR_{29}$; or a group selected from ($C_1$-$C_6$)alkyl, heterocycloalkyl, aryl, heteroaryl, —($C_1$-$C_6$)alkyl-aryl, and —($C_1$-$C_6$)alkyl-heterocycloalkyl, said group being optionally substituted with one or several groups selected from halo, heterocycle or —$OR_{32}$;

Z is a ($C_1$-$C_6$)alkyl;

$R_1$ to $R_4$ are, independently of one another, H, halo or —$OR_{51}$;

$R_5$ is H;

$R_6$ to $R_8$ are, independently of one another, H, halo, —$OR_{56}$, —$NR_{57}R_{58}$; or a group selected from $(C_1-C_6)$alkyl, heterocycloalkyl, aryl, heteroaryl, —$(C_1-C_6)$alkyl-aryl and —$(C_1-C_6)$alkyl-heterocycloalkyl, said group being optionally substituted with one or several groups selected from halo, —$OR_{79}$, —$NR_{80}R_{81}$, —$SR_{82}$, —$S(O)R_{83}$, —$SO_2R_{84}$, —$SO_2NR_{85}R_{86}$, —$OCOR_{87}$, —$NR_{88}COR_{89}$, —$NR_{90}C(O)OR_{91}$, —$CO_2R_{92}$, —$CONR_{93}R_{94}$, —$CO_2R_{95}$, —$OCONR_{96}R_{97}$, —$COR_{98}$, nitro (—$NO_2$), cyano (—CN), oxo (=O); preferably H, halo, —$OR_{56}$, —$NR_{57}R_{58}$; or a group selected from $(C_1-C_6)$alkyl, heterocycloalkyl, aryl and heteroaryl; and $R_9$ to $R_{98}$ are, independently of one another, H, halo, or a group selected from $(C_1-C_6)$alkyl, aryl, heteroaryl, heterocycloalkyl, —$(C_1-C_6)$alkyl-aryl;

proviso that: when

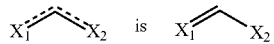

and Z is a methyl, Y is not a group selected from methyl or —$SO_2$-phenyl.

In another embodiment:

Y is —$C(O)NR_{10}R_{11}$; —$C(O)R_{12}$; —$S(O)_2R_{25}$; —$C(O)OR_{29}$ or —$SO_2$—$NR_{30}R_{31}$;

Z is a $(C_1-C_6)$alkyl and $R_1$ is H, halo, $(C_1-C_6)$alkyl, —$OR_{51}$, $CF_3$, —$NR_{52}R_{53}$, —$OS(O)_2NR_{54}R_{55}$ or —CN; or Z and $R_1$ together form a heterocycloalkyl;

$R_2$ to $R_4$ are, independently of one another, H, halo, $(C_1-C_6)$alkyl, —$OR_{51}$, —$CF_3$, —$NR_{52}R_{53}$, —$OS(O)_2NR_{54}R_{55}$ or —CN;

$R_5$ is H;

$R_6$ to $R_8$ are, independently of one another, H; halo; —$OR_{56}$; —$NR_{57}R_{58}$; —$C(O)NR_{59}R_{60}$; —$C(O)R_{61}$; —$R_{62}C(O)OR_{63}$; —$R_{64}C(O)R_{65}$; —$R_{66}NR_{67}R_{68}$; —$R_{69}OR_{70}$; —$S(O)_2R_{74}$; —$OR_{75}C(O)OR_{76}$; —OC(O)R_{77}$; —$C(O)OR_{78}$; or a group selected from $(C_1-C_6)$alkyl, heterocycloalkyl, aryl, heteroaryl, —$(C_1-C_6)$alkyl-aryl, —$(C_1-C_6)$alkyl-heterocycloalkyl, said group being optionally substituted with one or several groups selected from halo, —$OR_{79}$, —$NR_{80}R_{81}$, —$SR_{82}$, —$S(O)R_{83}$, —$SO_2R_{84}$, —$SO_2NR_{85}R_{86}$, —$OCOR_{87}$, —$NR_{88}COR_{89}$, —$NR_{90}C(O)OR_{91}$, —$CO_2R_{92}$, —$CONR_{93}R_{94}$, —$CO_2R_{95}$, —$OCONR_{96}R_{97}$, —$COR_{98}$, nitro (—$NO_2$), cyano (—CN), oxo (=O); and $R_{10}$ to $R_{12}$, $R_{25}$, $R_{29}$ to $R_{31}$ and $R_{51}$ to $R_{98}$ are, independently of one another, H; halo; or a group selected from $(C_1-C_6)$alkyl, aryl, heteroaryl, heterocycloalkyl, —$(C_1-C_6)$alkyl-aryl, said group being optionally substituted with one or several groups selected from halo, methyl, oxo (=O), and $SO_2$—$CH_3$;

or $R_{57}$-$R_{58}$, $R_{59}$-$R_{60}$, $R_{67}$-$R_{68}$, $R_{80}$-$R_{81}$, $R_{85}$-$R_{86}$, $R_{93}$-$R_{94}$, and/or $R_{96}$-$R_{97}$ respectively form together a heterocycloalkyl group;

with the proviso that: when

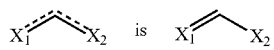

and Z is a methyl, Y is not —$SO_2$-phenyl.

In another particular embodiment:

Y is —$C(O)NR_{10}R_{11}$; —$C(O)R_{12}$; —$S(O)_2R_{25}$; —$C(O)OR_{29}$ or —$SO_2$—$NR_{30}R_{31}$;

Z is ethyl and $R_1$ is H, halo, methyl or OMe;

$R_2$ to $R_4$ are, independently of one another, H, halo, methyl or OMe;

$R_5$ is H;

$R_6$ to $R_8$ are, independently of one another, H, halo, —$OR_{56}$, —$NR_{57}R_{58}$; and $R_{10}$ to $R_{12}$, $R_{25}$, $R_{29}$ to $R_{31}$ and $R_{56}$ to $R_{58}$ are, independently of one another, H; halo; or a group selected from $(C_1-C_6)$alkyl, aryl, heteroaryl, heterocycloalkyl, —$(C_1-C_6)$alkyl-aryl, said group being optionally substituted with one or several groups selected from halo, $(C_1-C_6)$alkyl, —$C(O)R_{alk}$, —$C(O)OR_{alk}$, —$SO_2R_{alk}$, —$OR_{alk}$, —$COR_{alk}R_{alk}'$, oxo (=O), and $SO_2$-$R_{alk}$, wherein $R_{alk}$ and $R_{alk}'$ are, independently of each other, $(C_1-C_6)$alkyl, preferably selected from halo, methyl, oxo (=O), and $SO_2$—$CH_3$;

or $R_{57}$-$R_{58}$ form together a heterocycloalkyl group.

In particular, the compound of general formula (I) can be selected from compounds 1 to 36 described in the experimental part below and the pharmaceutically acceptable salts and solvates thereof.

More particularly, the compound of general formula (I) can be selected from compounds 7, 10, 17, 21, 26, and 32 to 36 described in the experimental part below and the pharmaceutically acceptable salts and solvates thereof.

According to one particular embodiment, the present invention is directed to the compound of general formula (I) as defined above, for use as a drug.

According to one particular embodiment, the present invention is directed to the compound of general formula (I) as defined above, for use as inhibitor of cellular necroptosis.

In particular, the present invention is directed to the compound of general formula (I) as defined above, for use for preventing and/or treating disorders associated with cellular necroptosis.

The present invention also relates to a method for inhibiting cellular necroptosis, comprising the administration to a person in need thereof of an effective dose of a compound of formula (I) as defined above. In particular, the present invention relates to a method for preventing and/or treating disorders associated with cellular necroptosis, comprising the administration to a person in need thereof of an effective dose of a compound of formula (I) as defined above The present invention also relates to the use of a compound of formula (I) as defined above, for the manufacture of a drug, in particular for inhibiting cellular necroptosis. In particular, the present invention also relates to the use of a compound of formula (I) as defined above, for the manufacture of a drug for preventing and/or treating disorders associated with cellular necroptosis.

The cellular necroptosis may be in particular tumour-cell-induced endothelial cell necroptosis.

The disorders associated with cellular necroptosis may be particularly trauma, hepatitis, ischemia reperfusion injury such as myocardial infarction and stroke, acute pancreatitis and acute tubular necrosis.

The disorders associated with cellular necroptosis can also be trauma in brain, hepatitis, alcoholic and non-alcoholic steatohepatitis, acute pancreatitis and acute tubular necrosis, heart or kidney transplantation, atherosclerosis, bone marrow failure, viral infection, Crohn's and ulcerative colitis, terminal ileitis, chronic obstructive pulmonary disease or ischemia reperfusion injury such as myocardial infarction or stroke.

The disorders associated with tumour-cell-induced endothelial cell necroptosis may be particularly tumour cells extravasation or metastasis.

The present invention also relates to a pharmaceutical composition comprising at least one compound of formula (I) as defined above and at least one pharmaceutically acceptable excipient.

According to one particular embodiment, the present invention is directed to the pharmaceutical composition as defined above, for use for inhibiting cellular necroptosis.

According to one particular embodiment, the present invention is directed to the pharmaceutical composition as defined above, for use for preventing and/or treating disorders associated with cellular necroptosis.

The present invention also relates to a method for inhibiting cellular necroptosis, comprising the administration to a person in need thereof of an effective dose of the pharmaceutical composition as defined above. In particular, the present invention relates to a method for preventing and/or treating disorders associated with cellular necroptosis, comprising the administration to a person in need thereof of an effective dose of the pharmaceutical composition as defined above.

The present invention also relates to the use of the pharmaceutical composition as defined above, for the manufacture of a drug, in particular for inhibiting cellular necroptosis. In particular, the present invention also relates to the use of the pharmaceutical composition as defined above, for the manufacture of a drug for preventing and/or treating disorders associated with cellular necroptosis.

The cellular necroptosis may be in particular tumour-cell-induced endothelial cell necroptosis.

The disorders associated with cellular necroptosis may be particularly trauma, hepatitis, ischemia reperfusion injury such as myocardial infarction and stroke, acute pancreatitis and acute tubular necrosis.

The disorders associated with cellular necroptosis can also be trauma in brain, hepatitis, alcoholic and non-alcoholic steatohepatitis, acute pancreatitis and acute tubular necrosis, heart or kidney transplantation, atherosclerosis, bone marrow failure, viral infection, Crohn's and ulcerative colitis, terminal ileitis, chronic obstructive pulmonary disease or ischemia reperfusion injury such as myocardial infarction or stroke.

The disorders associated with tumour-cell-induced endothelial cell necroptosis may be particularly tumour cells extravasation or metastasis.

The pharmaceutical compositions according to the invention may be formulated notably for oral administration or for injection, wherein said compositions are intended for mammals, including humans.

The pharmaceutical composition can be administered orally by means of tablets and gelatin capsules.

When a solid composition is prepared in the form of tablets, the main active ingredient is mixed with a pharmaceutical vehicle such as gelatin, starch, lactose, magnesium stearate, talc, gum arabic and the like. The tablets may be coated with sucrose or with other suitable materials, or they may be treated in such a way that they have a prolonged or delayed activity and they continuously release a predetermined amount of active principle.

A preparation in gelatin capsules is obtained by mixing the active ingredient with a diluent and pouring the mixture obtained into soft or hard gelatin capsules.

For administration by injection, aqueous suspensions, isotonic saline solutions or sterile and injectable solutions which contain pharmacologically compatible dispersing agents and/or wetting agents are used.

The active ingredient may be administered in unit dosage forms of administration, in mixture with standard pharmaceutical carriers, to animals or to humans. The compounds of the invention as active ingredients may be used in doses ranging between 0.01 mg and 1000 mg per day, given in a single dose once per day or administered in several doses throughout the day, for example twice a day in equal doses. The dose administered per day advantageously is between 5 mg and 500 mg, even more advantageously between 10 mg and 200 mg. It may be necessary to use doses outside these ranges as determined by the person skilled in the art.

The pharmaceutical compositions according to the invention may further comprise at least one other active ingredient, such as another cellular necroptosis inhibitor, or an apoptosis inhibitor, an autophagy inhibitor, a ferroptosis inhibitor, an inhibitor of MPT (The mitochondrial permeability transition) pore-dependent necrosis, a cyclophylin inhibitor, a Cyclin-dependent kinase 5 (CDK5) inhibitor, a parthanatos inhibitor, a thrombin inhibitor, an antioxidant (such as glutathione or allopurinol) or an inflammatory inhibitor.

The present invention relates also to a pharmaceutical composition comprising:
  (i) at least one compound of formula (I) or of formula (II) as defined above, and
  (ii) at least one other active ingredient, such as another cellular necroptosis inhibitor, or an apoptosis inhibitor, an autophagy inhibitor, a ferroptosis inhibitor, an inhibitor of MPT (The mitochondrial permeability transition) pore-dependent necrosis, a cyclophylin inhibitor, a Cyclin-dependent kinase 5 (CDK5) inhibitor, a parthanatos inhibitor, a thrombin inhibitor, an antioxidant (such as glutathione or allopurinol) or an inflammatory inhibitor,
as a combination product for simultaneous, separate or sequential use.

The present invention also relates to the use of a compound of general formula (I) as defined above; for the preservation and/or protection of biological materials such as cells, tissues, body fluids and organs, and of microorganisms, advantageously as a medical device.

In the context of the present invention, a medical device refers to any product which is put in contact with organs, tissues, cells or products from the human or animal body origin during their conservation, their preparation, their transformation, their packaging or their transport prior to their therapeutic use in humans. A medical device according to the present invention can also be any product coming into contact with embryos in the context of an activity of medically assisted procreation. In particular, this category of products includes graft preservation media (tissues, organs), the media used in the context of in vitro fertilization, or media used during the preparation of cell therapy products.

In particular, the present invention is directed to the use of a compound of general formula (I) as defined above, for use in medium for preserving organs, biological tissue, or living cells, preferably for preserving organs such as for example liver or kidney.

The compound of the invention can thus be used in the case of a graft as a supplementary therapeutic product for preserving cells, tissues or organs between the sampling on a donor and the graft on a receiver.

The inventors of the present invention have developed a process to prepare the compounds according to the invention. The present invention thus also relates to a process for preparing a compound of formula (I) as defined above, wherein Z is (C$_1$-C$_6$)alkyl, preferably ethyl, comprising the following steps:

i) reacting a 3-picoline with a 4-ethoxybenzonitrile to give a compound of following formula (II):

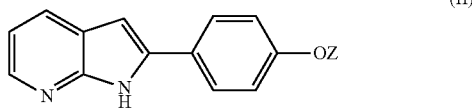

ii) then, reacting the compound of formula (II) with a compound of formula Y—W, wherein Y is as defined above and W is halo, in particular Cl, Br or I.

iii) optionally salifying and/or solvating the compound of formula (I) obtained in step ii) to give a pharmaceutically acceptable salt and/or solvate thereof.

Step i.:

Such a reaction can be carried out in conditions well-known to the person skilled in the part, notably in the presence of a strong base such as LDA. The solvent of this reaction may be tetrahydrofuran (THF).

Step ii):

Such a reaction can be carried out in conditions well-known to the person skilled in the part, notably by direct addition on azaindole nitrogen ring.

In particular, step ii) may be carried out in a solvent such as dichloromethane, dimethylformamide (DMF), dimethylsulfoxide (DMSO), N-methylpyrrolidone (NMP), THF, acetic anhydride or anhydrous toluene, or a mixture thereof.

The reaction of step ii) is advantageously performed in the presence of a base, in particular a strong base, such as triethylamine (Et$_3$N), diisopropylethylamine (DIPEA), 1,4-Diazabicyclo[2.2.2]octane (DABCO), sodium hydride (NaH), lithium diisopropylamide (LDA), lithium hexamethyldisilazane (LiHMDS), nbutyllithium, isopropylmagnesium chloride (iPrMgCl), potassium tertbutoxide (KOtBu), potassium carbonate (K$_2$CO$_3$), potassium hydroxide (KOH), sodium hydroxide (NaOH), cesium carbonate (Cs$_2$CO$_3$) or tripotassium phosphate (K$_3$PO$_4$).

Step ii) may also be carried out in the presence of a catalyst, such as copper iodide (CuI), Tetra-n-butylammonium iodide (nBu$_4$NI), dimethylaminopyridine (DMAP) or N,N'-dimethylethyldiamine.

Step iii):

The salification or solvatation step can be carried out by methods well known to the one skilled in the art, in particular by reaction of the compound of formula (I) obtained in step ii. with an organic or inorganic acid, an organic or inorganic base or a solvent, as defined previously.

The solvent can be notably the solvent used in the last step of the preparation of the compound according to the invention, in particular the solvent used in step ii.

Thus steps i) to iii) can be carried out in a single step, without isolating intermediate compounds.

At the end of step ii), both N1- and N7-substituted compounds are obtained in the reaction medium. These compounds can then be separated from the reaction medium by methods well known to the person skilled in the art, such as by extraction, evaporation of the solvent or by precipitation or crystallisation (followed by filtration).

Further protection/deprotection steps or functionalization steps can be carried out in the process described above, such steps and their reaction conditions being well known to the one skilled in the art.

The compound obtained can be separated from the reaction medium by methods well known to the person skilled in the art, such as by extraction, evaporation of the solvent or by precipitation or crystallisation (followed by filtration).

The compound can also be purified if necessary by methods well known to the person skilled in the art, such as by recrystallization, by distillation, by chromatography on a column of silica gel or by high performance liquid chromatography (HPLC).

According to another embodiment of the present invention, the N1-substituted compounds of general formula (I) can also be prepared according to the following process:

(i') reacting a 5-bromo-3-iodopyridin-2-amine with a 1-ethoxy-4-ethynylbenzene to give a compound of following formula (III):

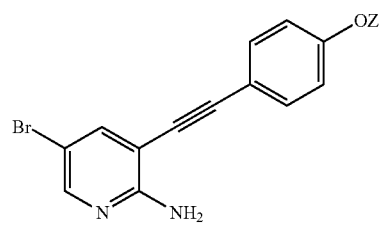

(ii') then, reacting the compound of formula (III) with a compound of formula Y—W, wherein Y is as defined above and W is halo, in particular Cl, Br or I, to obtained a compound of formula (IV):

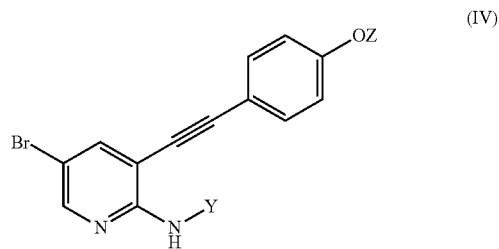

(iii') then, dissolving the compound of formula (IV) in anhydrous DMF and reacting the obtained solution with CuI;

(iv') optionally salifying and/or solvating the compound of formula (I) obtained in step iii') to give a pharmaceutically acceptable salt and/or solvate thereof.

Step (i'):

Such a reaction can be carried out in conditions well-known to the person skilled in the part, notably in the presence of a catalyst such as copper iodide (CuI) or Bis(triphenylphosphine)palladium(II) dichloride (PdCl$_2$(PPh$_3$)$_2$). The solvent of this reaction may be tetrahydrofuran (THF) toluene, dioxane or triethylamine (Et$_3$N).

Step (ii'):

Such a reaction can be carried out in conditions well-known to the person skilled in the part, notably by direct addition on azaindole nitrogen ring.

In particular, step (ii') may be carried out in a solvent such as dichloromethane, dimethylformamide (DMF), dimethylsulfoxide (DMSO), THF, acetic anhydride or anhydrous toluene, or a mixture thereof.

The reaction of step (ii') is advantageously performed in the presence of a base, in particular a strong base, such as triethylamine (Et$_3$N), pyridine, diisopropylethylamine (DIPEA), 1,4-Diazabicyclo[2.2.2]octane (DABCO), sodium hydride (NaH), potassium tertbutylate (KOtBu), n-butyllithium (nBuLi), lithium diisopropylamide (LDA), lithium hexamethyldisilazane (LiHMDS), potassium carbonate (K$_2$CO$_3$), potassium hydroxide (KOH), sodium hydroxide (NaOH), cesium carbonate (Cs$_2$CO$_3$) or tripotassium phosphate (K$_3$PO$_4$).

Step (iii'):

Such a reaction can be carried out in conditions well-known to the person skilled in the part, notably in a microwave reactor and in the presence of a catalyst such as copper iodide (CuI), tetra-n-butylammonium fluoride (TBAF), cesium carbonate (Cs$_2$CO$_3$) or palladium(II) dichloride (PdCl$_2$). The solvent of this reaction may be dimethylformamide (DMF), dimethylsulfoxide (DMSO) or N-methylpyrrolidone (NMP).

Step (iv'):

The salification or solvatation step can be carried out by methods well known to the one skilled in the art, in particular by reaction of the compound of formula (I) obtained in step (iii'). with an organic or inorganic acid, an organic or inorganic base or a solvent, as defined previously.

The solvent can be notably the solvent used in the last step of the preparation of the compound according to the invention, in particular the solvent used in step (ii').

Thus steps (I') to (iv') can be carried out in a single step, without isolating intermediate compounds.

Further protection/deprotection steps or functionalization steps can be carried out in the process described above, such steps and their reaction conditions being well known to the one skilled in the art.

The compound obtained can be separated from the reaction medium by methods well known to the person skilled in the art, such as by extraction, evaporation of the solvent or by precipitation or crystallisation (followed by filtration).

The compound can also be purified if necessary by methods well known to the person skilled in the art, such as by recrystallization, by distillation, by chromatography on a column of silica gel or by high performance liquid chromatography (HPLC).

The examples which follow illustrate the invention without limiting its scope in any way.

EXAMPLES

Figure 1:
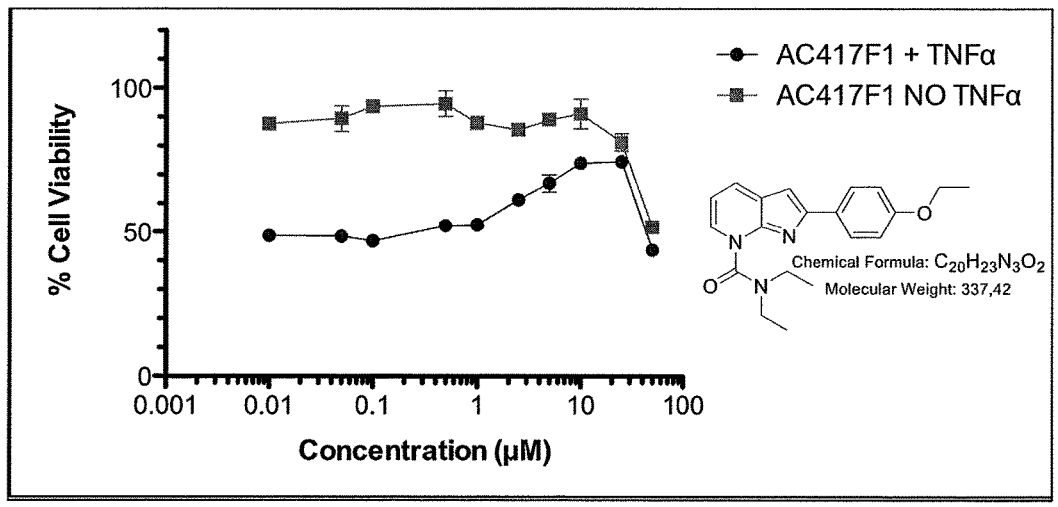
FIG. 1. represents the dose-dependent inhibition by compound 7 of necroptosis induced by TNF-α in human T lymphocyte (Jurkat FADD deficient cell line)
Figure 2:
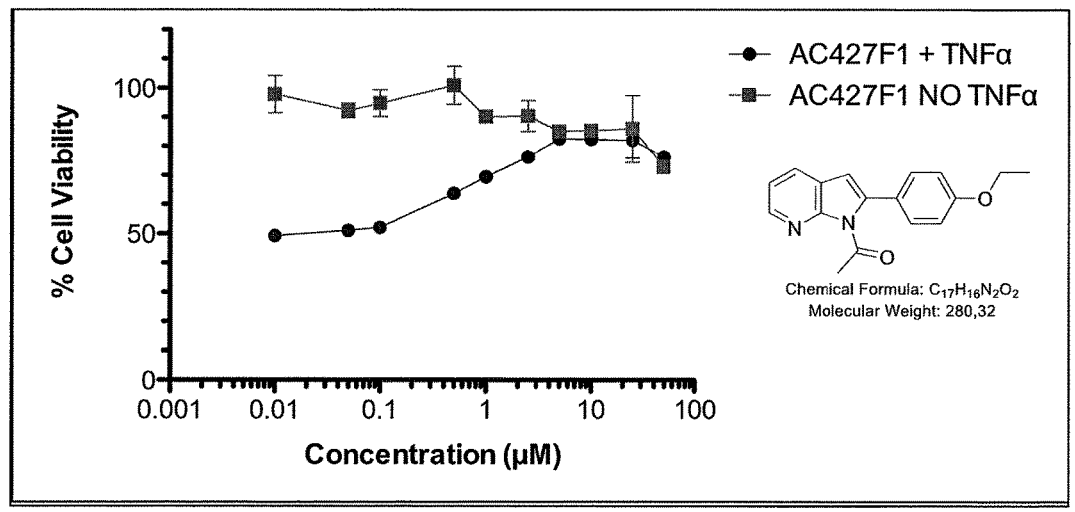
FIG. 2. represents the dose-dependent inhibition by compound 10 of necroptosis induced by TNF-α in human T lymphocyte (Jurkat FADD deficient cell line)
Figure 3:
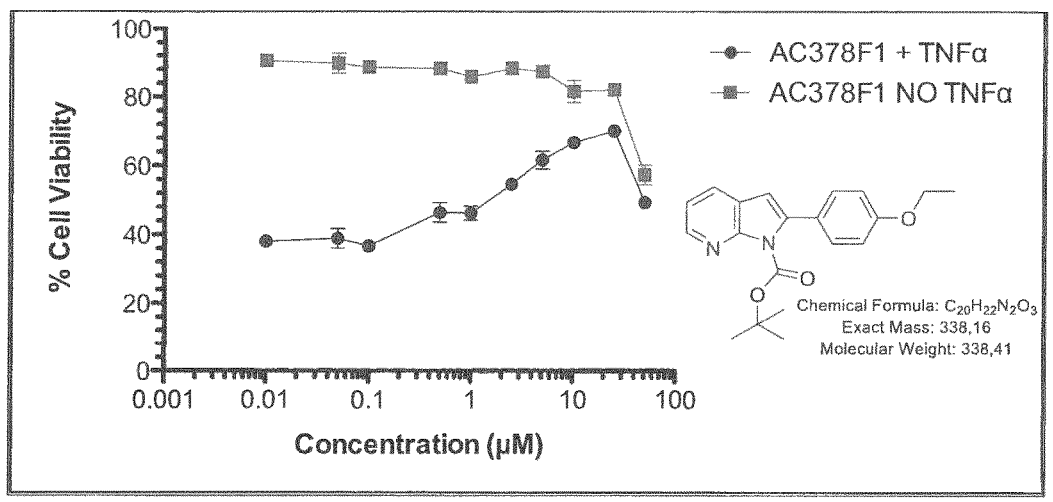
FIG. 3. represents the dose-dependent inhibition by compound 17 of necroptosis induced by TNF-α in human T lymphocyte (Jurkat FADD deficient cell line)
Figure 4:
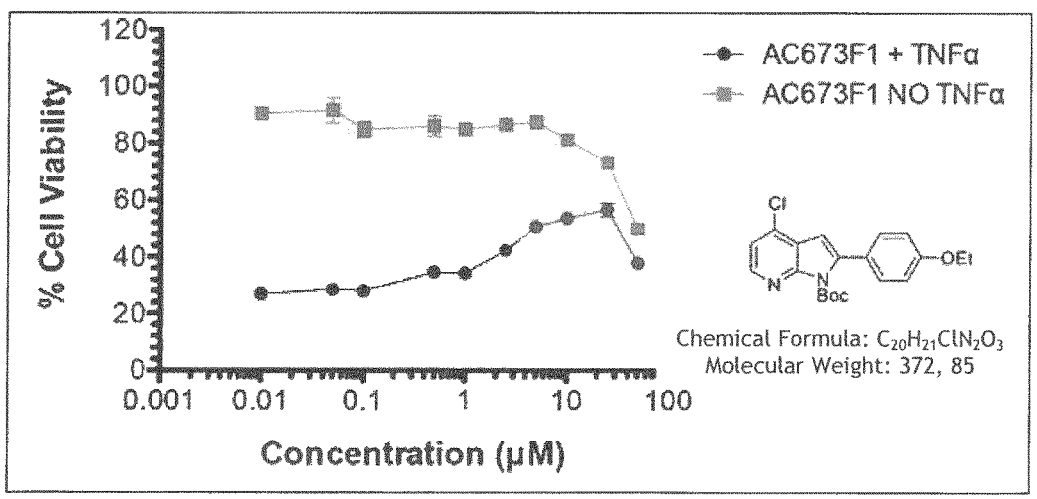
FIG. 4. represents the dose-dependent inhibition by compound 26 of necroptosis induced by TNF-α in human T lymphocyte (Jurkat FADD deficient cell line)

The following abbreviations have been used in the following examples:

BnBr: Bromure de benzyle
BOC: tert-butoxycarbonyle
Boc$_2$O: Dicarbonate de di-tert-butyle
BSA: Bovine Serum Albumin
d: doublet
DMAP: Dimethylaminopyridine
DMF: Dimethylformamide
DMSO: Dimethylsulfoxyde
DTT: Dithiothreitol
EC$_{50}$: Half maximal effective concentration
EDTA: Ethylenediaminetetraacetic acid
EGTA: Ethylene glycol-bis(β-aminoethyl ether)-N,N,N',N'-tetraacetic acid
EOMCl: Ethoxymethoxychloride
eq: equivalent
Et: Ethyl (CH$_2$CH$_3$)
EtOAc: Ethyl acetate
h: hour
$^1$H-: Protium
Hz: Hertz
IC$_{50}$: Half maximal inhibitory concentration
J: Coupling constant
kg: kilogram
LDA: Lithium diisopropylamide
LiHMDS: Lithium HexaMethylDiSilazide
m: multiplet
M: Molar
mCPBA: Meta-Chloroperoxybenzoic acid
Me: Methyl (CH$_3$)
mg: milligram
MHz: MegaHertz
min: minute(s)
ml: milliliter
mM: Millimolar
mmol: millimole
MOPS: 3-(N-morpholino)propanesulfonic acid
MsCl: Methanesulfonyl chloride
nBuLi: n-Butyllithium
ND: Not determined
NMR: Nuclear Magnetic Resonance
PMBCl: p-Methoxybenzyl chloride
q: Quadruplet
r.t: Room temperature
s: Simplet
SEMCl: 2-(Trimethylsilyl)ethoxymethyl chloride
Sib: Sibiriline
t: Triplet THF: Tetrahydrofuran
μg: microgram
μl: Microliter
μM: Micromolar I. Synthesis of the Compounds According to the Invention Example 1: Synthesis of N1 and N7-Substituted Sibs Selective Synthesis of N1-Substituted Derivatives (First Method)

Synthesis of 5-bromo-3-((4-ethoxyphenyl)ethynyl)pyridin-2-amine

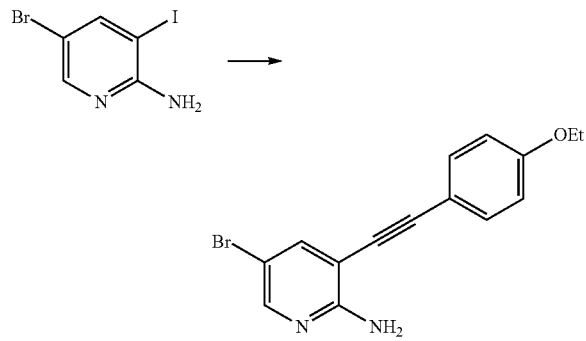

5-bromo-3-iodopyridin-2-amine (5 g, 16.7 mmol) was placed under argon and dissolved in anhydrous THF (50 ml). Et₃N (11.5 ml, 5 eq, 83 mmol) and 1-ethoxy-4-ethynylbenzene (2.93 g, 1.2 eq, 20 mmol) were added, followed by CuI (80 mg, 0.025 eq, 0.42 mmol) and PdCl₂(PPh₃)₂ (290 mg, 0.025 eq, 0.42 mmol). The dark brown mixture was stirred at r.t. for 3 h, before water (150 ml) and CH₂Cl₂ (150 ml) were added. The aqueous layer was extracted with CH₂Cl₂ and the organic extracts were washed with water and brine, dried over MgSO₄ and concentrated. The crude product was purified by flash chromatography (PE:EtOAc gradient 90:10 to 75:25) to afford the desired compound (4.6 g, 87%).

¹H-NMR (300 MHz, CDCl₃): 1.43 (t, J=7.0 Hz, 3H), 4.06 (q, J=7.0 Hz, 2H), 5.12 (bs, 2H), 6.84-7.03 (m, 2H), 7.38-7.53 (m, 2H), 7.68 (s, 1H), 8.17 (s, 1H).

Synthesis of 3-(5-bromo-3-((4-ethoxyphenyl)ethynyl)pyridin-2-yl)-1,1-diethylurea

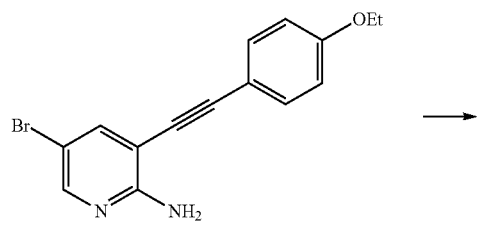

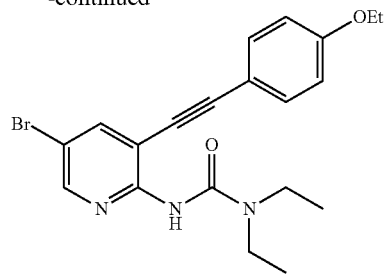

5-bromo-3-((4-ethoxyphenyl)ethynyl)pyridin-2-amine (100 mg, 31 mmol) was dissolved in anhydrous THF (5 ml), NaH (63 mg, 5 eq, 1.55 mmol) was added and the mixture was stirred for 10 min before addition of N,N-diethylcarbamoyl chloride (46 μL, 1.2 eq, 0.37 mmol). The reaction was stirred at r.t. for 16 h, quenched with water and extracted with EtOAc (2×10 ml). The organic layer was washed with brine, dried over MgSO₄, filtered and concentrated. The crude product was purified by flash chromatography (60:40 PE:EtOAc) to afford an off-white solid (72 mg, 55%).

¹H-NMR (300 MHz, CDCl₃): 1.24 (t, J=7.1 Hz, 6H), 1.45 (t, J=7.0 Hz, 3H), 3.43 (q, J=7.1 Hz, 4H), 4.08 (q, J=7.0 Hz, 2H), 6.84-6.93 (m, 2H), 7.38 (bs, 1H), 7.39-7.48 (m, 2H), 7.86 (s, 1H), 8.34 (s, 1H).

Synthesis of 5-bromo-2-(4-ethoxyphenyl)-N,N-diethyl-1H-pyrrolo[2,3-b]pyridine-1-carboxamide (Compound 1)

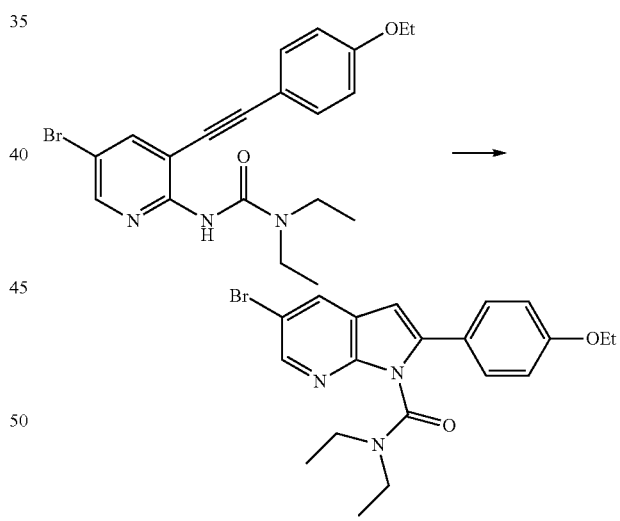

3-(5-bromo-3-((4-ethoxyphenyl)ethynyl)pyridin-2-yl)-1,1-diethylurea (70 mg, 0.17 mmol) was placed in a 2.5 ml microwave vial under argon and dissolved in anhydrous DMF (1 ml). CuI (64 mg, 2 eq, 0.34 mmol) was added and the mixture was stirred at 160° C. for 30 min in a Biotage Initiator microwave reactor. After cooling, the reaction was filtered, concentrated to dryness and the crude product was purified by flash chromatography (CH₂Cl₂:MeOH 95:5) to afford the desired compound (44 mg, 64%).

¹H-NMR (300 MHz, CDCl₃): 0.88 (t, J=7.1 Hz, 3H), 1.19 (t, J=7.1 Hz, 3H), 1.44 (t, J=7.0 Hz, 3H), 2.82-3.05 (m, 2H), 3.33 (dq, J=14.1, 7.1 Hz, 1H), 3.84 (dq, J=14.1, 7.1 Hz, 1H), 4.07 (q, J=7.0 Hz, 2H), 6.52 (s, 1H), 6.94 (d, J=8.8 Hz, 2H), 7.53 (d, J=8.8 Hz, 2H), 7.99 (d, J=2.1 Hz, 1H), 8.33 (d, J=2.1 Hz, 1H).

Selective Synthesis of N1-Substituted Derivatives
(Second Method)

Synthesis of
2-chloro-3-((4-ethoxyphenyl)ethynyl)pyridine

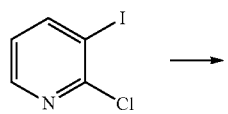

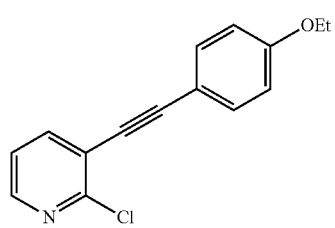

2-chloro-3-iodopyridine (500 mg, 2.09 mmol) was placed under argon and dissolved in anhydrous THF (10 ml). Et$_3$N (1.44 ml, 5 eq, 10 mmol) and 1-ethoxy-4-ethynylbenzene (365 mg, 1.2 eq, 2.5 mmol) were added, followed by CuI (10 mg, 0.025 eq, 0.05 mmol) and PdCl$_2$(PPh$_3$)$_2$ (37 mg, 0.025 eq, 0.05 mmol). The dark brown mixture was stirred at r.t. for 3 h, before water (20 ml) and CH$_2$Cl$_2$ (20 ml) were added. The aqueous layer was extracted with CH$_2$Cl$_2$ and the organic extracts were washed with water and brine, dried over MgSO$_4$ and concentrated. The crude product was purified by flash chromatography (PE:EtOAc 85:15) to afford the desired compound (440 mg, 82%). $^1$H-NMR (300 MHz, CDCl$_3$): 1.43 (t, J=7.0 Hz, 3H), 4.06 (q, J=7.0 Hz, 2H), 6.87 (d, J=8.8 Hz, 2H), 7.22 (dd, J=7.7, 4.8 Hz, 1H), 7.49 (d, J=8.8 Hz, 2H), 7.82 (dd, J=7.7, 1.9 Hz, 1H), 8.31 (dd, J=4.8, 1.9 Hz, 1H).

General Procedure for Synthesis of N1-heteroaryl
Compounds from
2-chloro-3-((4-ethoxyphenyl)ethynyl)pyridine 2-chloro-3-((4-ethoxyphenyl)ethynyl)pyridine (50 mg, 0.19 mmol) was charged into a vial with Pd$_2$dba$_3$ (18 mg, 0.1 eq, 0.019 mmol), XantPhos (22 mg, 0.2 eq, 0.036 mmol), Cs$_2$CO$_3$ (189 mg, 3 eq, 0.58 mmol) and the corresponding heterocyclic amine (1.3 eq, 0.25 mmol). The vial was placed under argon and anhydrous dioxane was added before stirring 16 h at 100° C. After cooling the reaction was diluted with EtOAc, filtered on a pad of Celite® and concentrated. The crude product was purified by flash chromatography to afford the desired compound.

Synthesis of 2-(4-ethoxyphenyl)-1-(pyrazin-2-yl)-H-pyrrolo[2,3-b]pyridine (Compound 2)

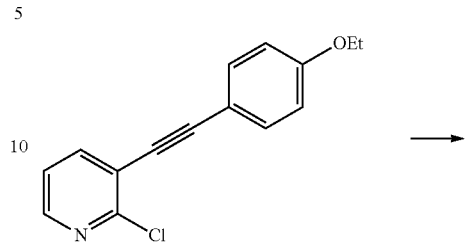

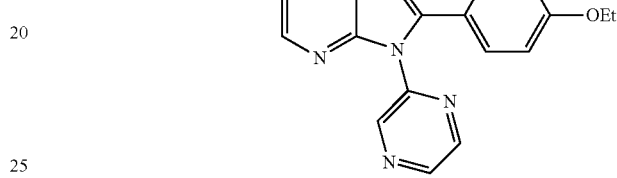

Following the general procedure with 2-aminopyrazine (33 mg, 54%). $^1$H-NMR (300 MHz, CDCl$_3$): 1.40 (t, J=7.0 Hz, 3H), 4.02 (q, J=7.0 Hz, 2H), 6.70 (s, 1H), 6.79-6.84 (m, 2H), 7.12-7.21 (m, 3H), 7.95 (dd, J=7.8, 1.6 Hz, 1H), 8.31 (dd, J=4.8, 1.6 Hz, 1H), 8.51-8.53 (m, 2H), 8.82 (d, J=0.8 Hz, 1H).

Synthesis of 2-(4-ethoxyphenyl)-1-(pyrimidin-2-yl)-1H-pyrrolo[2,3-b]pyridine (Compound 3)

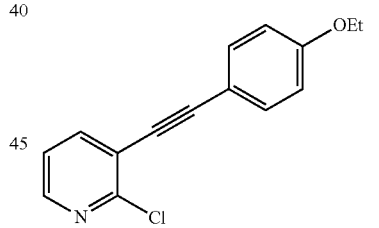

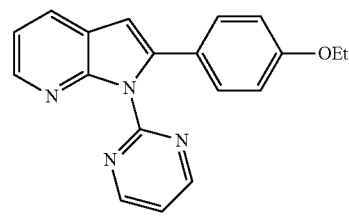

Following the general procedure with 2-aminopyrimidine (36 mg, 60%). $^1$H-NMR (300 MHz, CDCl$_3$): 1.40 (t, J=7.0 Hz, 3H), 4.02 (q, J=7.0 Hz, 2H), 6.68 (s, 1H), 6.79-6.83 (m, 2H), 7.12-7.19 (m, 3H), 7.38 (bs, 1H), 7.95 (d, J=7.7 Hz, 1H), 8.38 (s, 1H), 8.84 (s, 2H).

Synthesis of 2-(2-(4-ethoxyphenyl)-1H-pyrrolo[2,3-b]pyridin-1-yl)-1,3,4-thiadiazole (Compound 4)

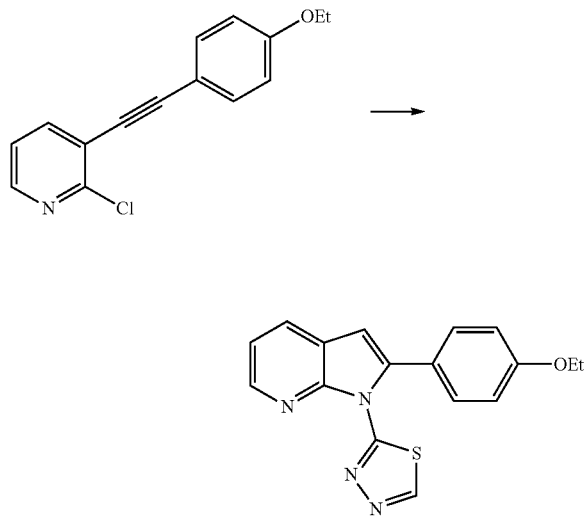

Following the general procedure with 2-amino-1,3,4-thiadiazole (37 mg, 59%). $^1$H-NMR (300 MHz, CDCl$_3$): 1.42 (t, J=7.0 Hz, 3H), 4.05 (q, J=7.0 Hz, 2H), 6.69 (s, 1H), 6.85-6.95 (m, 2H), 7.23 (dd, J=7.8, 4.8 Hz, 1H), 7.30-7.37 (m, 2H), 7.94 (dd, J=7.8, 1.3 Hz, 1H), 8.37 (dd, J=4.8, 1.3 Hz, 1H), 9.09 (s, 1H).

Synthesis of 2-(4-ethoxyphenyl)-1-(5-nitropyridin-2-yl)-1H-pyrrolo[2,3-b]pyridine (Compound 5)

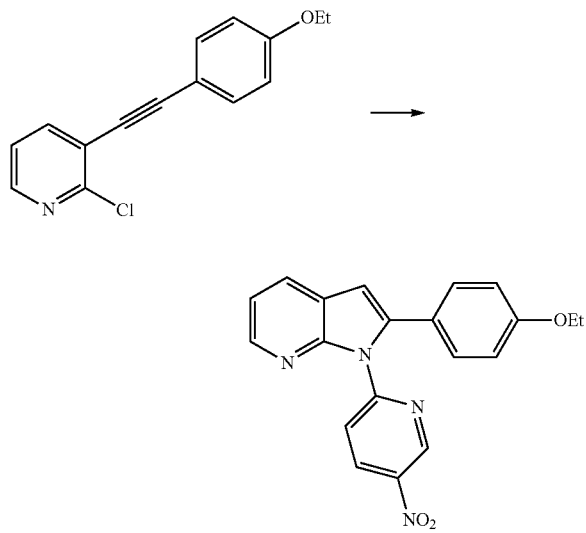

Following the general procedure with 2-amino-5-nitropyridine (17 mg, 24%). $^1$H-NMR (300 MHz, CDCl$_3$): 1.45 (t, J=7.0 Hz, 3H), 4.06 (q, J=7.0 Hz, 2H), 6.74 (s, 1H), 6.81-6.90 (m, 2H), 7.15-7.28 (m, 3H), 7.95-8.02 (m, 2H), 8.34 (d, J=4.1 Hz, 1H), 8.63 (dd, J=8.9, 2.8 Hz, 1H), 9.27 (d, J=2.4 Hz, 1H).

Synthesis of 4-(6-(2-(4-ethoxyphenyl)-1H-pyrrolo[2,3-b]pyridin-1-yl)pyrimidin-4-yl)morpholine (Compound 6)

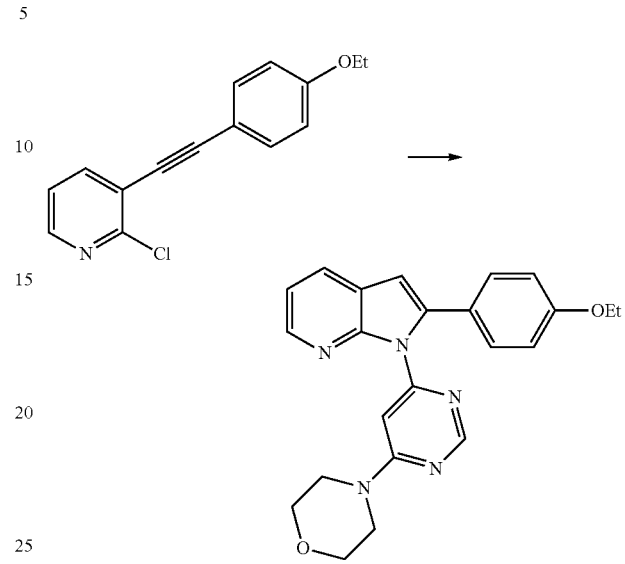

Following the general procedure with 6-morpholinopyrimidin-4-amine (18 mg, 22%).
$^1$H-NMR (300 MHz, DMSO-d$_6$): 1.75 (t, J=7.0 Hz, 3H), 3.95-4.01 (m, 4H), 4.08-4.15 (m, 4H), 4.36 (t, J=7.0 Hz, 2H), 7.01 (s, 1H), 7.12 (s, 1H), 7.11-7.22 (m, 2H), 7.48-7.59 (m, 1H), 7.58-7.63 (m, 2H), 8.30 (d, J=7.6 Hz, 1H), 8.68 (d, J=3.9 Hz, 1H), 8.85 (s, 1H).

Synthesis of N1- and N7-Substituted Derivatives by Direct Addition on Azaindole Nitrogen Ring

Synthesis of 2-(4-ethoxyphenyl)-1H-pyrrolo[2,3-b]pyridine

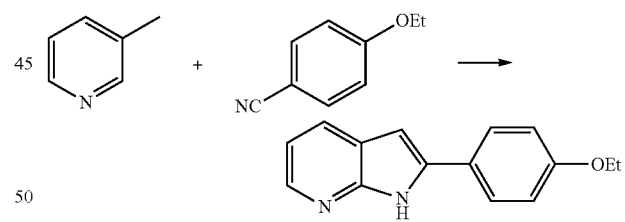

LDA was freshly prepared by adding dropwise a nBuLi solution in hexanes (54 ml, 2.5 M, 135 mmol) under argon to a diisopropylamine (19 ml, 135 mmol) solution in anhydrous THF (150 ml) at −5° C. and stirring for 20 min. Then a solution of 3-picoline (7 g, 75 mmol, 1 eq) in anhydrous THF (100 ml) was added dropwise at 0° C. and the orange mixture was stirred for 20 min before dropwise addition of a solution of 4-ethoxybenzonitrile (11.1 g, 75 mmol, 1 eq) in anhydrous THF (100 ml). After 1 h at 0° C., more LDA solution in THF (150 ml) was added dropwise (135 mmol, prepared from 54 ml nBuLi and 19 ml diisopropylamine) and the reaction was slowly warmed to r.t during 1 h before being heated to reflux in a water bath for 2 h. After cooling, the yellow solution was quenched carefully with saturated NH$_4$Cl (100 ml) and water (250 ml) was added. The precipitate was filtered, washed with diethyl ether and water, dried under vacuum to afford a light yellow solid (11 g, 61%).

$^1$H-NMR (300 MHz, DMSO-d$_6$): 1.35 (t, J=7.1 Hz, 3H), 4.07 (q, J=7.1 Hz, 2H), 6.78 (d, J=2.2 Hz, 1H), 7.00-7.05 (m, 3H), 7.85-7.89 (m, 3H), 8.15 (dd, J=4.7, 1.6 Hz, 1H), 12.0 (bs, 1H).

Synthesis of 2-(4-ethoxyphenyl)-1H-pyrrolo[2,3-b]pyridine-7-oxide

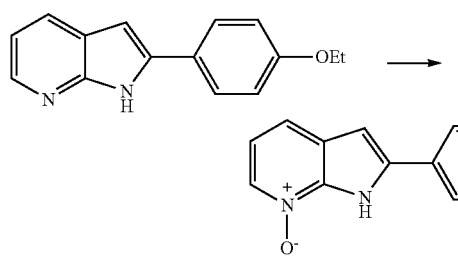

2-(4-ethoxyphenyl)-1H-pyrrolo[2,3-b]pyridine (2 g, 8.4 mmol) was suspended in a mixture of EtOAc (10 ml) and hexane (40 ml) under argon and cooled to 0° C. mCPBA (2.7 g, 12.6 mmol, 1.5 eq) was added in portion, the reaction was slowly warmed to r.t. and stirred for 12 h. The solvent was removed under vacuum and the residue was suspended in saturated K$_2$CO$_3$ solution (50 ml), stirred vigorously for 30 min, filtered and washed with water to obtain a yellow solid that was dried under vacuum (1.5 g, 70%).

$^1$H-NMR (300 MHz, DMSO-d$_6$): 1.35 (t, J=7.1 Hz, 3H), 4.08 (q, J=7.1 Hz, 2H), 6.92 (s, 1H), 6.99-7.09 (m, 3H), 7.56 (d, J=7.1 Hz, 1H), 7.96 (d, J=8.8 Hz, 2H), 8.08 (d, J=6.3 Hz, 1H), 12.7 (bs, 1H).

Synthesis of 4-chloro-2-(4-ethoxyphenyl)-1H-pyrrolo[2,3-b]pyridine

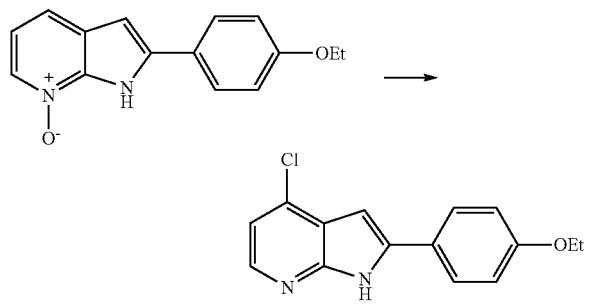

2-(4-ethoxyphenyl)-1H-pyrrolo[2,3-b]pyridine-7-oxide (1 g, 4.1 mmol) was dissolved in anhydrous DMF (10 ml) under argon and MsCl was added dropwise (487 μl, 6.15 mmol, 1.5 eq). The reaction was heated to 80° C. and stirred for 6 h before cooling with an ice bath to yield a precipitate. Water (40 ml) was added and the yellow solid was filtered, washed with more water and dried under vacuum (696 mg, 65%).

$^1$H-NMR (300 MHz, DMSO-d$_6$): 1.35 (t, J=7.0 Hz, 3H), 4.09 (q, J=7.0 Hz, 2H), 6.85 (d, J=2.1 Hz, 1H), 7.02 (d, J=8.8 Hz, 2H), 7.17 (d, J=5.2 Hz, 1H), 7.92 (d, J=8.8 Hz, 2H), 8.12 (d, J=5.2 Hz, 1H), 12.39 (bs, 1H).

Synthesis of 2-(4-ethoxyphenyl)-N,N-diethyl-7H-pyrrolo[2,3-b]pyridine-7-carboxamide (Compound 7)

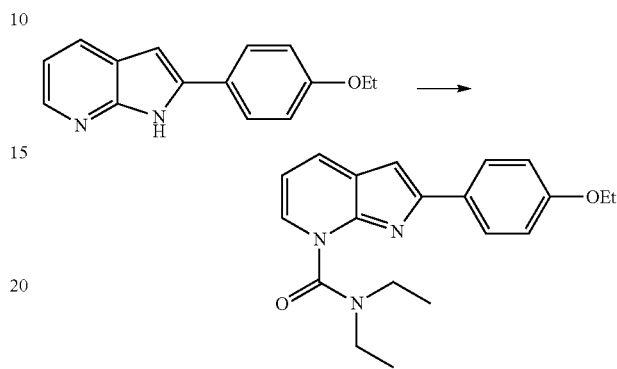

2-(4-ethoxyphenyl)-1H-pyrrolo[2,3-b]pyridine (50 mg, 0.21 mmol) was dissolved in anhydrous DMF (2 ml) under argon and treated with NaH (42 mg, 5 eq, 1.05 mmol) and stirred at r.t. for 15 min before adding N,N-diethylcarbamoyl chloride (32 μL, 1.2 eq, 0.25 mmol). The mixture was stirred 12 h at r.t., quenched with water and extracted with EtOAc (2×10 ml). The organic layer was washed with brine, dried over MgSO$_4$, filtered and concentrated. The crude product was purified by flash chromatography (60:40 PE:EtOAc) to afford a brown solid (30 mg, 45%).

$^1$H-NMR (300 MHz, CDCl$_3$): 1.08 (t, J=7.0 Hz, 3H), 1.40-1.52 (m, 6H), 3.10-3.21 (m, 2H), 3.65-3.86 (m, 2H), 4.08 (d, J=7.0 Hz, 2H), 6.83 (dd, J=7.3, 6.4 Hz, 1H), 6.88 (s, 1H), 6.94 (d, J=8.9 Hz, 2H), 7.58 (dd, J=6.4, 1.1 Hz, 1H), 7.95 (dd, J=7.3, 1.1 Hz, 1H), 8.00-8.08 (m, 2H).

Synthesis of 2-(4-ethoxyphenyl)-7-(4-methoxybenzyl)-7H-pyrrolo[2,3-b]pyridine and 2-(4-ethoxyphenyl)-1-(4-methoxybenzyl)-1H-pyrrolo[2,3-b]pyridine (Compounds 8 and 9)

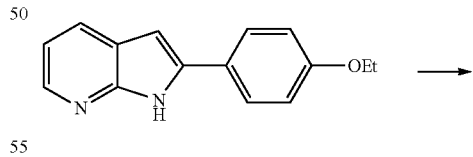

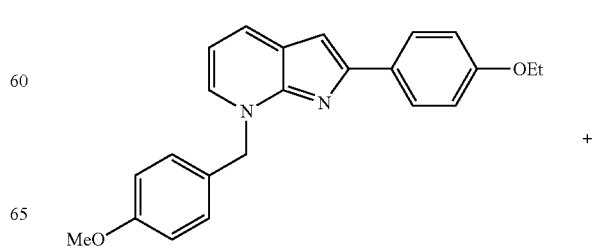

+

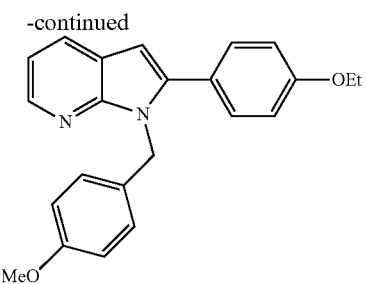

2-(4-ethoxyphenyl)-1H-pyrrolo[2,3-b]pyridine (50 mg, 0.21 mmol) was dissolved in anhydrous DMF (2 ml) under argon, nBu₄NI (8 mg, 0.1 eq, 0.021 mmol) was added and the reaction was treated with NaH (42 mg, 5 eq, 1.05 mmol) and stirred at r.t. for 15 min before adding PMBCl (36 mg, 1.1 eq, 0.23 mmol). The mixture was stirred 12 h at r.t., quenched with water and extracted with EtOAc (2×10 ml). The organic layer was washed with brine, dried over MgSO₄, filtered and concentrated. The crude product was purified by flash chromatography (80:20 PE:EtOAc) to afford the N1-regioisomer as a yellow oil (15 mg, 19%). The elution was continued (60:40 PE:EtOAc) to obtain the N7-regioisomer as a yellow oil (16 mg, 20%).

¹H-NMR (300 MHz, CDCl₃) for N1-substituted compound: 1.44 (t, J=7.0 Hz, 3H), 3.73 (s, 3H), 4.07 (q, J=7.0 Hz, 2H), 5.48 (s, 2H), 6.48 (s, 1H), 6.65-6.79 (m, 2H), 6.83-6.97 (m, 4H), 7.09 (dd, J=7.8, 4.8 Hz, 1H), 7.20-7.39 (m, 2H), 7.90 (dd, J=7.8, 1.6 Hz, 1H), 8.33 (dd, J=4.7, 1.6 Hz, 1H).

¹H-NMR (300 MHz, CDCl₃) for N7-substituted compound: 1.45 (t, J=7.0 Hz, 3H), 3.81 (s, 3H), 4.10 (q, J=7.0 Hz, 2H), 5.85 (s, 2H), 6.72 (dd, J=7.4, 6.3 Hz, 1H), 6.83-6.90 (m, 2H), 6.91 (s, 1H), 6.97 (d, J=8.9 Hz, 2H), 7.39 (dd, J=6.3, 1.1 Hz, 1H), 7.44 (d, J=8.7 Hz, 2H), 7.90 (dd, J=7.4, 1.1 Hz, 1H), 8.11 (d, J=8.9 Hz, 2H).

Synthesis of 1-(2-(4-ethoxyphenyl)-1H-pyrrolo[2,3-b]pyridin-1-yl)ethan-1-one (Compound 10)

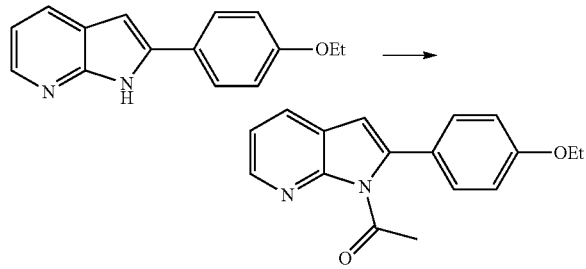

2-(4-ethoxyphenyl)-1H-pyrrolo[2,3-b]pyridine (50 mg, 0.21 mmol) was suspended in acetic anhydride (0.5 ml) under argon, DMAP (5 mg) was added, followed by Et₃N (45 μL, 1.5 eq, 0.31 mmol) and the mixture was stirred at 70° C. for 72 h before quenching with saturated NaHCO₃. The reaction was partitioned between EtOAc and water and the organic layer was washed with brine, dried over MgSO₄, filtered and concentrated. The crude product was purified by flash chromatography (90:10 PE:EtOAc) to afford a white solid (18 mg, 31%).

¹H-NMR (300 MHz, CDCl₃): 1.44 (t, J=7.0 Hz, 3H), 3.06 (s, 3H), 4.08 (q, J=7.0 Hz, 2H), 6.52 (s, 1H), 6.92-6.95 (m, 2H), 7.19 (dd, J=7.8, 4.8 Hz, 1H), 7.32-7.38 (m, 2H), 7.84 (dd, J=7.8, 1.7 Hz, 1H), 8.35 (dd, J=4.8, 1.7 Hz, 1H).

Synthesis of 4-(2-(2-(4-ethoxyphenyl)-7H-pyrrolo[2,3-b]pyridin-7-yl)ethyl)morpholine and 4-(2-(2-(4-ethoxyphenyl)-1H-pyrrolo[2,3-b]pyridin-1-yl)ethyl)morpholine (Compounds 11 and 12)

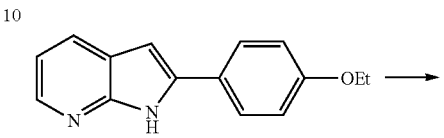

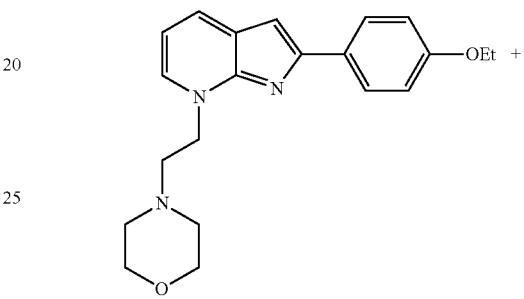

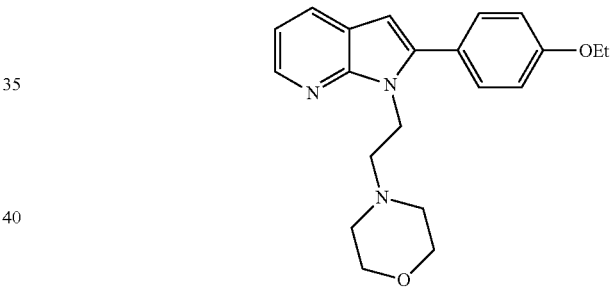

2-(4-ethoxyphenyl)-1H-pyrrolo[2,3-b]pyridine (50 mg, 0.21 mmol) was dissolved in anhydrous DMF (2 ml) under argon, treated with K₂CO₃ (145 mg, 5 eq, 1.05 mmol) and stirred at r.t. for 15 min before adding 4-(2-Chloroethyl)morpholine hydrochloride (58 mg, 1.5 eq, 0.32 mmol). The mixture was stirred 18 h at 70° C., concentrated under vacuum and the residue was purified by flash chromatography (98:2 CH₂Cl₂:MeOH) to afford the N1-regioisomer as a yellow oil (19 mg, 26%). The elution was continued (92:8 CH₂Cl₂:MeOH) to obtain the N7-regioisomer as a yellow oil (27 mg, 36%).

¹H-NMR (300 MHz, CDCl₃) for N1-substituted compound: 1.46 (t, J=7.0 Hz, 3H), 2.23-2.39 (m, 4H), 2.63 (t, J=6.9 Hz, 2H), 3.46-3.62 (m, 4H), 4.10 (q, J=7.0 Hz, 2H), 4.46 (t, J=6.9 Hz, 2H), 6.41 (s, 1H), 6.95-7.03 (m, 2H), 7.06 (dd, J=7.8, 4.8 Hz, 1H), 7.44-7.51 (m, 2H), 7.87 (dd, J=7.8, 1.6 Hz, 1H), 8.30 (dd, J=4.8, 1.6 Hz, 1H).

¹H-NMR (300 MHz, CDCl₃) for N7-substituted compound: 1.44 (t, J=7.0 Hz, 3H), 2.53-2.62 (m, 4H), 3.03 (t, J=6.3 Hz, 2H), 3.64-3.72 (m, 4H), 4.04-4.15 (q, J=7.0 Hz, 2H), 4.84 (t, J=6.3 Hz, 2H), 6.76-6.83 (m, 1H), 6.87 (s, 1H), 6.92-7.00 (m, 2H), 7.57 (dd, J=7.4, 1.0 Hz, 1H), 7.95 (dd, J=7.4, 1.0 Hz, 1H), 8.03-8.10 (m, 2H).

Synthesis of 1-benzyl-2-(4-ethoxyphenyl)-1H-pyrrolo[2,3-b]pyridine and 7-benzyl-2-(4-ethoxyphenyl)-7H-pyrrolo[2,3-b]pyridine (Compounds 13 and 14)

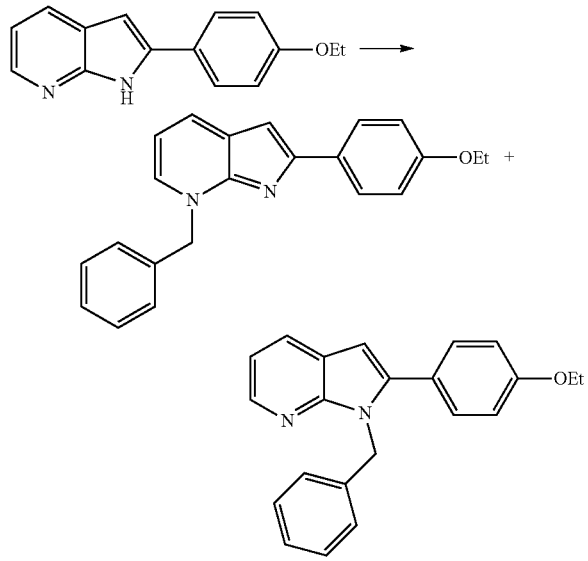

2-(4-ethoxyphenyl)-1H-pyrrolo[2,3-b]pyridine (50 mg, 0.21 mmol) was dissolved in anhydrous DMF (2 ml) under argon, treated with powdered KOH (35 mg, 3 eq, 0.63 mmol) and stirred at r.t. for 15 min before adding BnBr (30 μL, 1.2 eq, 0.25 mmol). The mixture was stirred 12 h at r.t., quenched with saturated NH$_4$Cl and extracted with CH$_2$Cl$_2$ (2×10 ml). The organic layer was washed with brine, dried over MgSO$_4$, filtered and concentrated. The crude product was purified by flash chromatography (90:10 PE:EtOAc) to afford the N1-regioisomer as a yellow oil (25 mg, 36%). The elution was continued (60:40 PE:EtOAc) to obtain the N7-regioisomer as a yellow solid (26 mg, 38%).

$^1$H-NMR (300 MHz, CDCl$_3$) for N1-substituted compound: 1.44 (t, J=7.0 Hz, 3H), 4.06 (q, J=7.0 Hz, 2H), 5.55 (s, 2H), 6.50 (s, 1H), 6.85-6.91 (m, 2H), 6.96-6.98 (m, 2H), 7.14 (dd, J=7.4, 5.0 Hz, 1H), 7.14-7.22 (m, 3H), 7.28-7.33 (m, 2H), 7.92 (dd, J=7.8, 1.6 Hz, 1H), 8.32 (dd, J=4.7, 1.6 Hz, 1H).

$^1$H-NMR (300 MHz, CDCl$_3$) for N7-substituted compound: 1.45 (t, J=7.0 Hz, 3H), 4.10 (q, J=7.0 Hz, 2H), 5.92 (s, 2H), 6.72 (dd, J=7.4, 6.3 Hz, 1H), 6.93 (s, 1H), 6.95-7.03 (m, 2H), 7.31-7.51 (m, 6H), 7.91 (dd, J=7.4, 1.1 Hz, 1H), 8.07-8.18 (m, 2H).

Synthesis of 2-(4-ethoxyphenyl)-1-(2-(pyrrolidin-1-yl)ethyl)-1H-pyrrolo[2,3-b]pyridine and 2-(4-ethoxyphenyl)-7-(2-(pyrrolidin-1-yl)ethyl)-7H-pyrrolo[2,3-b]pyridine (Compounds 15 and 16)

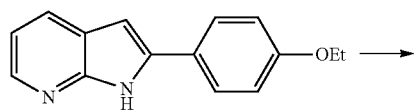

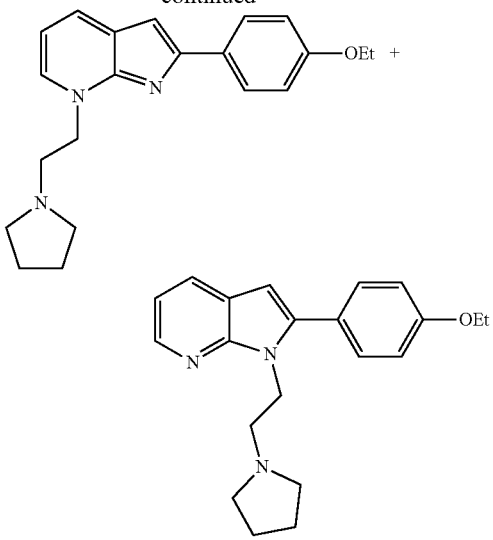

2-(4-ethoxyphenyl)-1H-pyrrolo[2,3-b]pyridine (50 mg, 0.21 mmol) was dissolved in anhydrous DMF (2 ml) under argon, treated with Cs$_2$CO$_3$ (342 mg, 5 eq, 1.05 mmol) and stirred at r.t. for 15 min before adding 1-(2-Chloroethyl)pyrrolidine hydrochloride (54 mg, 1.5 eq, 0.32 mmol). The mixture was stirred 18 h at 70° C., concentrated under vacuum and the residue was purified by flash chromatography (90:10 CH$_2$Cl$_2$:MeOH) to afford the N1-regioisomer as a yellow oil (13 mg, 19%). The elution was continued (88:10:2 CH$_2$Cl$_2$:MeOH:AcOH) to obtain the N7-regioisomer as a yellow oil (7 mg, 10%).

$^1$H-NMR (300 MHz, CDCl$_3$) for N1-substituted compound: 1.46 (t, J=7.0 Hz, 3H), 1.78 (bm, 4H), 2.65 (bm, 4H), 2.94 (t, J=7.4 Hz, 2H), 4.10 (q, J=7.0 Hz, 2H), 4.46-4.71 (m, 2H), 6.41 (s, 1H), 6.96-7.05 (m, 2H), 7.07 (dd, J=7.8, 4.8 Hz, 1H), 7.37-7.50 (m, 2H), 7.86 (dd, J=7.8, 1.6 Hz, 1H), 8.30 (dd, J=4.8, 1.6 Hz, 1H).

$^1$H-NMR (300 MHz, CDCl$_3$) for N7-substituted compound: 1.43 (t, J=7.0, 3H), 1.81 (bm, 4H), 2.67 (bm, 4H), 3.21 (t, J=6.6 Hz, 2H), 4.09 (d, J=7.0 Hz, 2H), 4.87 (t, J=6.6 Hz, 2H), 6.73-6.82 (m, 1H), 6.87 (s, 1H), 6.95 (d, J=8.8 Hz, 2H), 7.62 (d, J=7.9 Hz, 1H), 7.93 (d, J=7.4 Hz, 1H), 8.07 (d, J=8.8 Hz, 2H).

Synthesis of tert-butyl 2-(4-ethoxyphenyl)-1H-pyrrolo[2,3-b]pyridine-1-carboxylate (Compound 17)

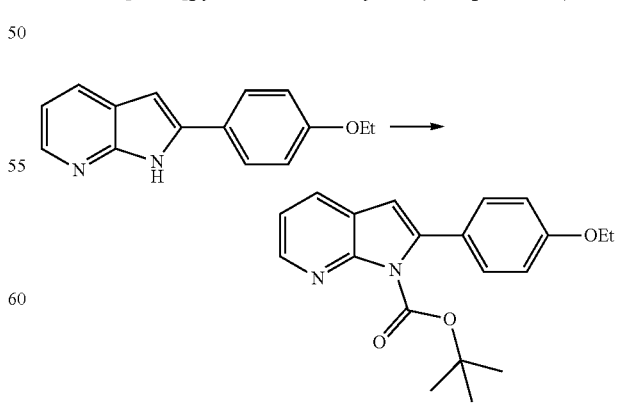

2-(4-ethoxyphenyl)-1H-pyrrolo[2,3-b]pyridine (100 mg, 0.42 mmol) was suspended in anhydrous CH$_2$Cl$_2$ (5 ml)

under argon, DMAP (5 mg) was added, followed by Et₃N (64 μL, 1.1 eq, 0.46 mmol) and Boc₂O (100 mg, 1.1 eq, 0.46 mmol) and the mixture was stirred at r.t. for 4 h before adding water. The organic layer was washed with brine, dried over MgSO₄, filtered and concentrated. The crude product was purified by flash chromatography (85:15 PE:EtOAc) to afford a white solid (92 mg, 65%).

¹H-NMR (300 MHz, CDCl₃): 1.31 (s, 9H), 1.44 (t, J=7.0 Hz, 3H), 4.08 (q, J=7.0 Hz, 2H), 6.43 (s, 1H), 6.86-7.01 (m, 2H), 7.17 (dd, J=7.8, 4.8 Hz, 1H), 7.31-7.41 (m, 2H), 7.84 (dd, J=7.8, 1.6 Hz, 1H), 8.48 (dd, J=4.8, 1.6 Hz, 1H).

Synthesis of ethyl 2-(2-(4-ethoxyphenyl)-1H-pyrrolo[2,3-b]pyridin-1-yl)acetate and ethyl 2-(2-(4-ethoxyphenyl)-7H-pyrrolo[2,3-b]pyridin-7-yl)acetate (Compounds 18 and 19)

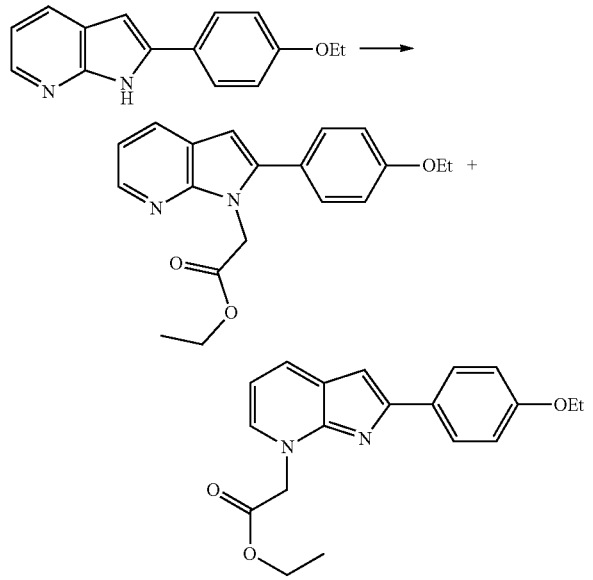

2-(4-ethoxyphenyl)-1H-pyrrolo[2,3-b]pyridine (50 mg, 0.21 mmol) was dissolved in anhydrous DMF (2 ml) under argon, treated with powdered KOH (35 mg, 3 eq, 0.63 mmol) and stirred at r.t. for 15 min before adding ethyl bromoacetate (28 μL, 1.2 eq, 0.25 mmol). The mixture was stirred 18 h at r.t., concentrated under vacuum and the residue was purified by flash chromatography (CH₂Cl₂) to afford the N1-regioisomer as a brown solid (10 mg, 15%). The elution was continued (98:2 CH₂Cl₂:MeOH) to obtain the N7-regioisomer as a yellow solid (18 mg, 26%).

¹H-NMR (300 MHz, CDCl₃) for N1-substituted compound: 1.21 (t, J=7.1 Hz, 3H), 1.45 (t, J=7.0 Hz, 3H), 4.09 (q, J=7.0 Hz, 2H), 4.17 (q, J=7.1 Hz, 2H), 5.00 (s, 2H), 6.49 (s, 1H), 6.94-7.01 (m, 2H), 7.11 (dd, J=7.8, 4.8 Hz, 1H), 7.35-7.42 (m, 2H), 7.91 (dd, J=7.8, 1.5 Hz, 1H), 8.31 (dd, J=4.8, 1.5 Hz, 1H).

¹H-NMR (300 MHz, CDCl₃) for N7-substituted compound: 1.31 (t, J=7.1 Hz, 3H), 1.40 (t, J=6.9 Hz, 3H), 4.08 (q, J=6.9 Hz, 2H), 4.29 (q, J=7.1 Hz, 2H), 5.75 (s, 2H), 6.87 (s, 1H), 6.91-7.02 (m, 3H), 7.59 (d, J=5.9 Hz, 1H), 8.01-8.06 (m, 3H).

Synthesis of 1-(ethoxymethyl)-2-(4-ethoxyphenyl)-1H-pyrrolo[2,3-b]pyridine (Compound 20)

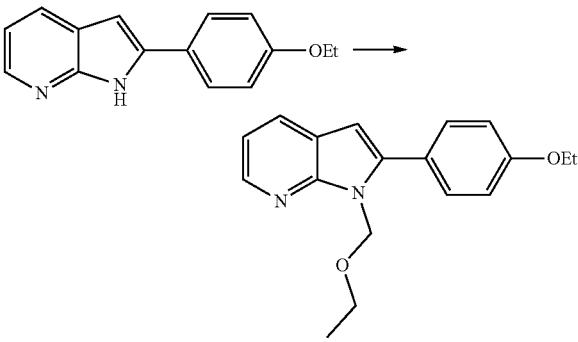

2-(4-ethoxyphenyl)-1H-pyrrolo[2,3-b]pyridine (100 mg, 0.42 mmol) was dissolved in anhydrous THF (5 ml) under argon and treated with NaH (84 mg, 5 eq, 2.1 mmol) and stirred at r.t. for 15 min before adding EOMCl (46 μL, 1.2 eq, 0.50 mmol). The mixture was stirred 12 h at r.t., quenched with water and extracted with EtOAc (2×10 ml). The organic layer was washed with brine, dried over MgSO₄, filtered and concentrated. The crude product was purified by flash chromatography (80:20 PE:EtOAc) to afford a white solid (47 mg, 38%).

¹H-NMR (300 MHz, CDCl₃): 1.31-1.16 (t J=7.0 Hz, 3H), 1.46 (t, J=7.0 Hz, 3H), 3.71 (q, J=7.0 Hz, 2H), 4.10 (q, J=7.0 Hz, 2H), 5.69 (s, 2H), 6.53 (s, 1H), 6.94-7.06 (m, 2H), 7.14 (dd, J=7.8, 4.9 Hz, 1H), 7.63-7.77 (m, 2H), 7.92 (d, J=7.8 Hz, 1H), 8.33 (dd, J=4.9, 1.5 Hz, 1H).

Synthesis of benzyl 2-(4-ethoxyphenyl)-7H-pyrrolo[2,3-b]pyridine-7-carboxylate (Compound 21)

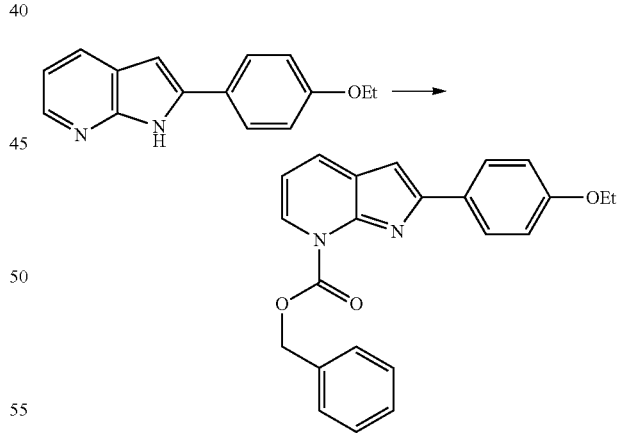

2-(4-ethoxyphenyl)-1H-pyrrolo[2,3-b]pyridine (50 mg, 0.21 mmol) was dissolved in anhydrous DMF (2 ml) under argon, treated with powdered KOH (35 mg, 3 eq, 0.63 mmol) and stirred at r.t. for 15 min before adding benzyl chloroformate (36 μL, 1.2 eq, 0.25 mmol). The mixture was stirred 18 h at r.t., concentrated under vacuum and the residue was purified by flash chromatography (CH₂Cl₂) to afford a brown solid (13 mg, 17%).

¹H-NMR (300 MHz, CDCl₃): 1.44 (t, J=7.0 Hz, 3H), 4.10 (q, J=7.0 Hz, 2H), 5.93 (s, 2H), 6.74 (dd, J=7.3, 6.4 Hz, 1H), 6.92 (s, 1H), 6.97 (d, J=8.9 Hz, 2H), 7.31-7.50 (m, 6H), 7.92 (dd, J=7.4, 1.0 Hz, 1H), 8.11 (d, J=8.9 Hz, 2H).

Synthesis of 2-(2-(4-ethoxyphenyl)-1H-pyrrolo[2,3-b]pyridin-1-yl)-N,N-dimethylethan-1-amine (Compound 22)

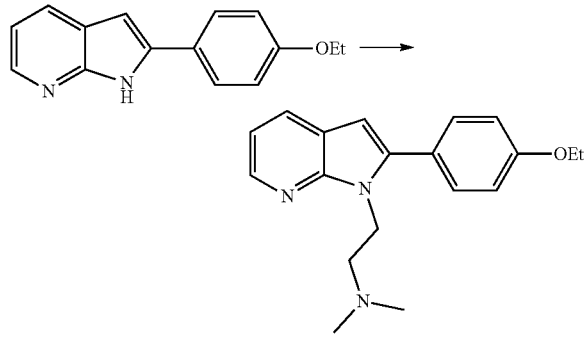

2-(4-ethoxyphenyl)-1H-pyrrolo[2,3-b]pyridine (100 mg, 0.42 mmol) was dissolved in anhydrous DMF (5 ml) under argon, treated with NaH (84 mg, 5 eq, 2.1 mmol) and stirred at r.t. for 15 min before adding 2-Chloro-N,N-dimethylethylamine hydrochloride (120 mg, 2 eq, 0.84 mmol). The mixture was stirred 12 h at 80° C., quenched with water and extracted with EtOAc (4×10 ml). The organic layer was washed with brine, dried over MgSO$_4$, filtered and concentrated. The crude product was purified by flash chromatography (90:10 EtOAc:MeOH) to afford a white solid (33 mg, 25%).

$^1$H-NMR (300 MHz, DMSO-d$_6$): 1.37 (t, J=6.9 Hz, 3H), 2.00 (s, 6H), 2.43 (t, J=7.0 Hz, 2H), 4.09 (q, J=6.9 Hz, 2H), 4.39 (t, J=7.0 Hz, 2H), 6.47 (s, 1H), 7.04-7.17 (m, 3H), 7.49-7.59 (m, 2H), 7.93 (dd, J=7.8, 1.6 Hz, 1H), 8.26 (dd, J=4.7, 1.6 Hz, 1H).

Synthesis of 2-(4-ethoxyphenyl)-1-((2-(trimethylsilyl)ethoxy)methyl)-1H-pyrrolo[2,3-b]pyridine (Compound 23)

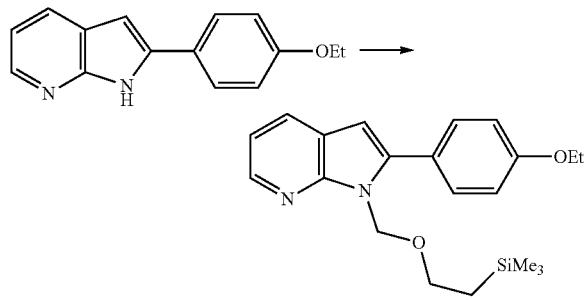

2-(4-ethoxyphenyl)-1H-pyrrolo[2,3-b]pyridine (150 mg, 0.63 mmol) was dissolved in anhydrous THF (5 ml) under argon and treated with NaH 126 mg, 5 eq, 3.2 mmol) and stirred at r.t. for 15 min before adding SEMCl (127 µL, 1.2 eq, 0.76 mmol). The mixture was stirred 12 h at r.t., quenched with water and extracted with EtOAc (2×10 ml). The organic layer was washed with brine, dried over MgSO$_4$, filtered and concentrated. The crude product was purified by flash chromatography (90:10 PE:EtOAc) to afford a clear oil (166 mg, 72%).

$^1$H-NMR (300 MHz, CDCl$_3$): −0.04 (s, 9H), 0.93-1.01 (m, 2H), 1.46 (t, J=7.0 Hz, 4H), 3.65-3.85 (m, 2H), 4.10 (q, J=7.0 Hz, 2H), 5.66 (s, 2H), 6.51 (s, 1H), 7.00 (d, J=8.9 Hz, 2H), 7.10 (dd, J=7.8, 4.8 Hz, 1H), 7.71 (d, J=8.9 Hz, 2H), 7.87 (dd, J=7.8, 1.6 Hz, 1H), 8.32 (dd, J=4.8, 1.6 Hz, 1H).

Synthesis of 2-(4-ethoxyphenyl)-1-methyl-1H-pyrrolo[2,3-b]pyridine (Compound 24)

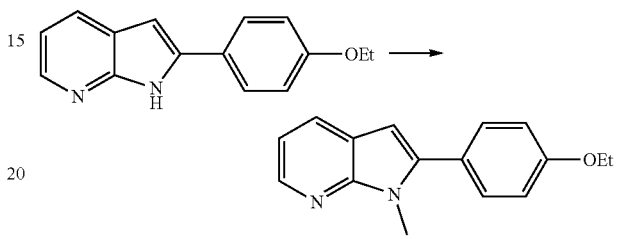

2-(4-ethoxyphenyl)-1H-pyrrolo[2,3-b]pyridine (100 mg, 0.42 mmol) was dissolved in anhydrous DMF (5 ml) under argon, treated with NaH (50 mg, 3 eq, 1.26 mmol) and stirred at r.t. for 15 min before adding MeI (53 µl, 2 eq, 0.84 mmol). The mixture was stirred 12 h, quenched with water and extracted with EtOAc (2×10 ml). The organic layer was washed with brine, dried over MgSO$_4$, filtered and concentrated. The crude product was purified by flash chromatography (85:15 PE:EtOAc) to afford a white solid (55 mg, 50%).

$^1$H-NMR (300 MHz, CDCl$_3$): 1.46 (t, J=7.0 Hz, 3H), 3.87 (s, 3H), 4.10 (q, J=7.0 Hz, 2H), 6.46 (s, 1H), 6.94-7.04 (m, 2H), 7.08 (dd, J=7.8, 4.8 Hz, 1H), 7.41-7.51 (m, 2H), 7.89 (dd, J=7.8, 1.6 Hz, 1H), 8.33 (dd, J=4.8, 1.6 Hz, 1H).

Synthesis of 2-(4-ethoxyphenyl)-7-methyl-7H-pyrrolo[2,3-b]pyridine (Compound 25)

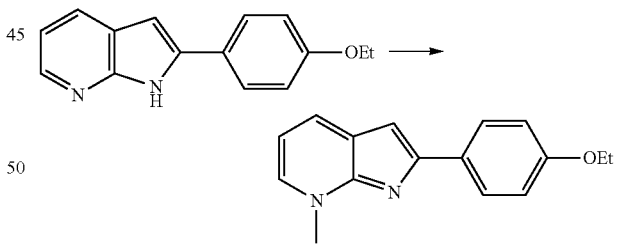

2-(4-ethoxyphenyl)-1H-pyrrolo[2,3-b]pyridine (50 mg, 0.21 mmol) was dissolved in anhydrous THF (2 ml) under argon, treated with MeI (0.5 ml, 40 eq, 80 mmol) and stirred at reflux for 1 h. After cooling, the solution was concentrated under vacuum to give the hydroiodide salt as a yellow powder that was dissolved in CH$_2$Cl$_2$. Aqueous ammonia (10 ml) was added and the biphasic mixture was stirred for 30 min before separation of the organic layer and extraction with CH$_2$Cl$_2$ (2×10 ml). The organic extracts were washed with brine, dried over MgSO$_4$, filtered and concentrated. The crude product was purified by flash chromatography (90:10 CH$_2$Cl$_2$:MeOH) to afford a yellow solid (27 mg, 51%).

1H-NMR (300 MHz, DMSO-d$_6$): 1.35 (t, J=7.0 Hz, 3H), 4.07 (q, J=7.0 Hz, 2H), 4.25 (s, 3H), 6.84-6.92 (m, 2H), 6.92-7.00 (m, 2H), 7.96 (d, J=6.0 Hz, 1H), 8.02-8.05 (m, 3H).

Synthesis of tert-butyl 4-chloro-2-(4-ethoxyphenyl)-1H-pyrrolo[2,3-b]pyridine-1-carboxylate (Compound 26)

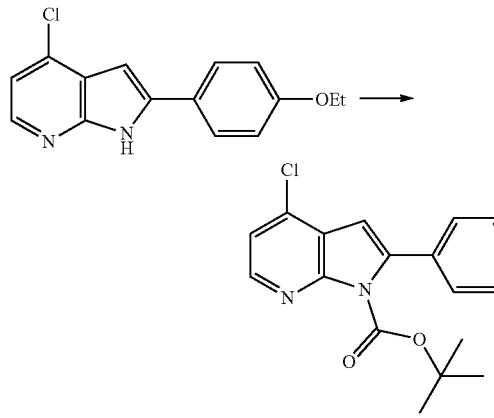

4-chloro-2-(4-ethoxyphenyl)-1H-pyrrolo[2,3-b]pyridine (50 mg, 0.18 mmol) was suspended in anhydrous $CH_2Cl_2$ (5 ml) under argon, DMAP (5 mg) was added, followed by $Et_3N$ (28 µL, 1.1 eq, 0.20 mmol) and $Boc_2O$ (43 mg, 1.1 eq, 0.20 mmol) and the mixture was stirred at r.t. for 4 h before adding water. The organic layer was washed with brine, dried over $MgSO_4$, filtered and concentrated. The crude product was purified by flash chromatography (90:10 PE:EtOAc) to afford a white solid (45 mg, 71%).

$^1$H-NMR (300 MHz, $CDCl_3$): 1.32 (s, 9H), 1.45 (t, J=7.0 Hz, 3H), 4.09 (q, J=7.0 Hz, 2H), 6.56 (s, 1H), 6.96 (d, J=8.8 Hz, 2H), 7.21 (d, J=5.3 Hz, 1H), 7.36 (d, J=8.8 Hz, 2H), 8.36 (d, J=5.3 Hz, 1H).

Synthesis of 2-(4-ethoxyphenyl)-1-(thiophen-2-yl)-1H-pyrrolo[2,3-b]pyridine (Compound 27)

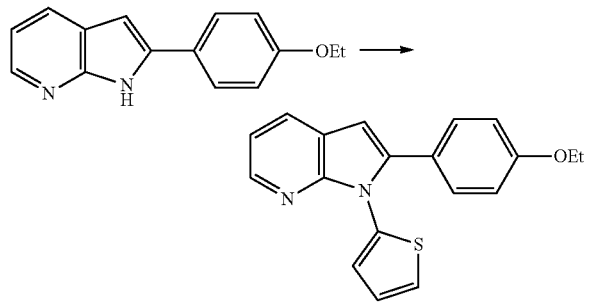

2-(4-ethoxyphenyl)-1H-pyrrolo[2,3-b]pyridine (50 mg, 0.21 mmol) was charged into a pressure tube with CuI (4 mg, 0.1 eq, 0.02 mmol), N,N'-Dimethylethylenediamine (5 µL, 0.2 eq, 0.04 mmol) and $K_3PO_4$ (94 mg, 2.1 eq, 0.44 mmol). The tube was placed under argon, anhydrous toluene (1 ml) was added followed by 2-iodothiophene (27 µL, 1.2 eq, 0.25 mmol) and the mixture was stirred at 120° C. for 2 days. The resulting solution was cooled to r.t., diluted with water and extracted with EtOAc (2×10 ml). The organic layer was washed with brine, dried over $MgSO_4$, filtered and concentrated. The crude product was purified by flash chromatography (70:30 PE:EtOAc) to afford a brown solid (5 mg, 7%).

$^1$H-NMR (300 MHz, $CDCl_3$): 1.41 (t, J=7.0 Hz, 3H), 4.03 (q, J=7.0 Hz, 2H), 6.64 (s, 1H), 6.79-6.89 (m, 2H), 6.95 (dd, J=3.7, 1.4 Hz, 1H), 7.00 (dd, J=5.5, 3.7 Hz, 1H), 7.14 (dd, J=7.8, 4.8 Hz, 1H), 7.25 (dd, J=5.5; 1.4 Hz, 1H), 7.28-7.34 (m, 2H), 7.91 (dd, J=7.8, 1.6 Hz, 1H), 8.34 (dd, J=4.8, 1.6 Hz, 1H).

Synthesis of 2-(4-ethoxyphenyl)-1-(pyridin-2-yl)-1H-pyrrolo[2,3-b]pyridine (Compound 28)

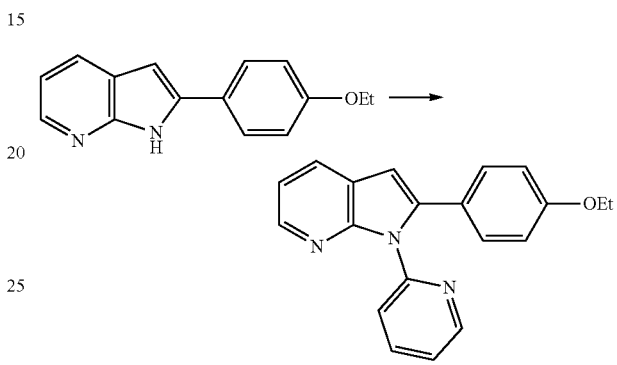

2-(4-ethoxyphenyl)-1H-pyrrolo[2,3-b]pyridine (50 mg, 0.21 mmol) was charged into a pressure tube with CuI (4 mg, 0.1 eq, 0.02 mmol), N,N'-Dimethylethylenediamine (5 µL, 0.2 eq, 0.04 mmol) and $K_3PO_4$ (94 mg, 2.1 eq, 0.44 mmol). The tube was placed under argon, anhydrous toluene (1 ml) was added followed by 2-iodopyridine (27 µL, 1.2 eq, 0.25 mmol) and the mixture was stirred at 120° C. for 2 days. The resulting solution was cooled to r.t., diluted with water and extracted with EtOAc (3×10 ml). The organic layer was washed with brine, dried over $MgSO_4$, filtered and concentrated. The crude product was purified by flash chromatography (98:2 $CH_2Cl_2$:MeOH) to afford a yellow oil (40 mg, 61%).

$^1$H-NMR (300 MHz, $CDCl_3$): 1.40 (t, J=7.0 Hz, 3H), 4.01 (q, J=7.0 Hz, 2H), 6.67 (s, 1H), 6.75-6.85 (m, 2H), 7.13 (dd, J=7.8, 4.8 Hz, 1H), 7.16-7.20 (m, 1H), 7.24-7.30 (m, 1H), 7.47 (dt, J=8.0, 0.8 Hz, 1H), 7.79 (dt, J=1.9, 7.6 Hz, 1H), 7.93 (dd, J=7.8, 1.6 Hz, 1H), 8.31 (dd, J=4.8, 1.6 Hz, 1H), 8.56 (ddd, J=4.9, 1.9, 0.8 Hz, 1H).

Synthesis of methyl 2-(4-ethoxyphenyl)-7H-pyrrolo[2,3-b]pyridine-7-carboxylate (Compound 29)

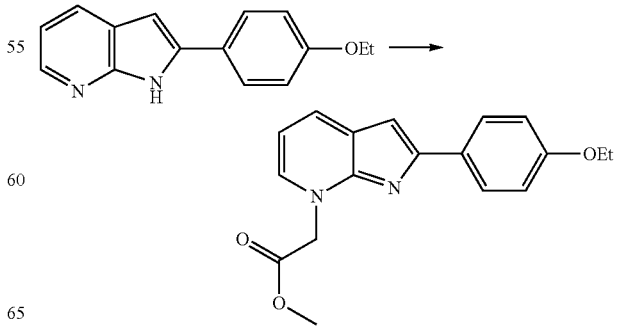

2-(4-ethoxyphenyl)-1H-pyrrolo[2,3-b]pyridine (50 mg, 0.21 mmol) was suspended in methyl bromoacetate (2 ml) under argon and stirred at 150° C. in a preheated oil bath for 15 min before cooling and filtration of the precipitate. The resulting brown solid was suspended in a saturated $K_2CO_3$ solution and stirred for 30 min before filtration. The residue was purified by flash chromatography ($CH_2Cl_2$:MeOH 98:2) to afford a yellow solid (20 mg, 32%).

$^1$H-NMR (300 MHz, $CDCl_3$): 1.43 (t, J=7.0 Hz, 3H), 3.81 (s, 3H), 4.08 (q, J=7.0 Hz, 2H), 5.64 (s, 2H), 6.86-6.88 (m, 2H), 6.95 (d, J=8.7 Hz, 2H), 7.50 (d, J=6.2 Hz, 1H), 7.99 (d, J=7.4 Hz, 1H), 8.06 (d, J=8.7 Hz, 2H).

Synthesis of Compounds 30 and 31

The following compounds can be prepared according to the same procedures as described previously for the synthesis of compounds 1 to 29.

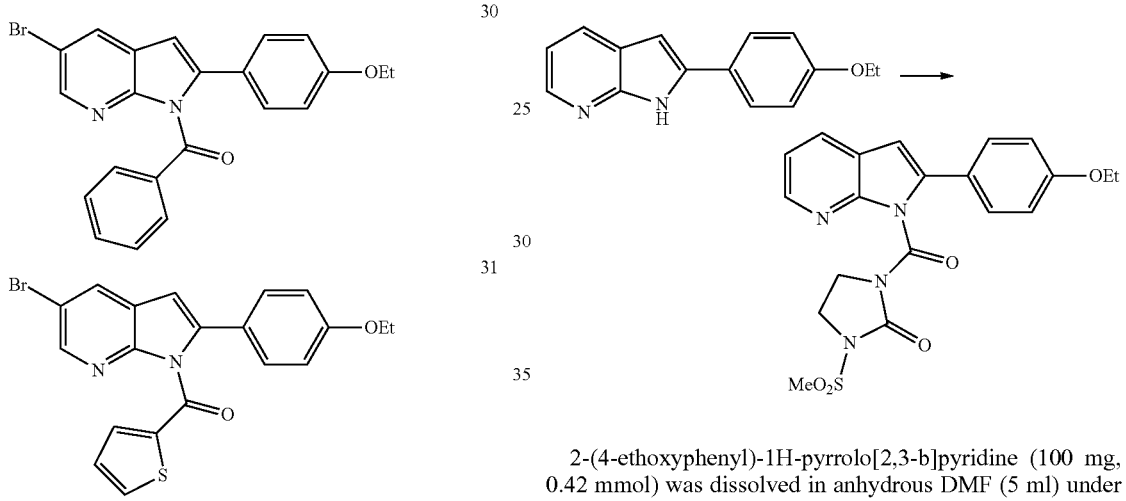

30

31

Synthesis of 2,2,2-trichloroethyl 2-(4-ethoxyphenyl)-1H-pyrrolo[2,3-b]pyridine-1-carboxylate (Compound 32)

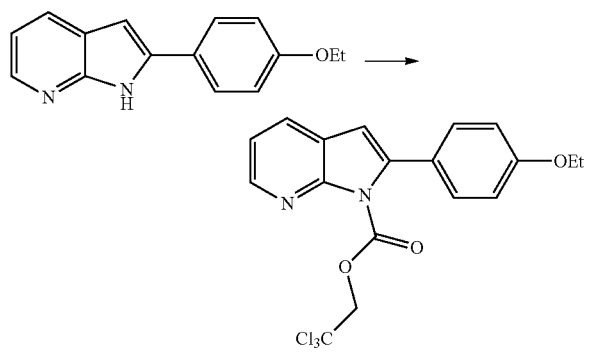

2-(4-ethoxyphenyl)-1H-pyrrolo[2,3-b]pyridine (100 mg, 0.42 mmol) was dissolved in anhydrous THF (5 ml) under argon, treated with LiHMDS (1M in toluene, 503 µL, 1.2 eq, 0.50 mmol) and stirred at 0° C. for 15 min before adding 2,2,2-trichloroethyl chloroformate (70 µL, 1.2 eq, 0.50 mmol). The mixture was stirred 24 h at r.t. and more electrophile was added (140 µL, 2.4 eq, 100 mmol). After 24 h of stirring at r.t., the reaction was quenched with water and extracted with EtOAc (4×10 ml). The organic layer was washed with brine, dried over $MgSO_4$, filtered and concentrated. The crude product was purified by flash chromatography (80:20 PE:EtOAc) to afford a yellow oil (27 mg, 15%).

$^1$H-NMR (300 MHz, $CDCl_3$): 1.36 (t, J=7.0 Hz, 3H), 4.00 (q, J=7.0 Hz, 2H), 4.82 (s, 2H), 6.47 (s, 1H), 6.86 (d, J=8.8 Hz, 2H), 7.19 (dd, J=7.8, 5.0 Hz, 2H), 7.31 (d, J=8.8 Hz, 2H), 7.82 (dd, J=7.8, 1.6 Hz, 1H), 8.43 (dd, J=5.0, 1.6 Hz, 1H).

Synthesis of 1-(2-(4-ethoxyphenyl)-1H-pyrrolo[2,3-b]pyridine-1-carbonyl)-3-(methylsulfonyl) imidazolidin-2-one (Compound 33)

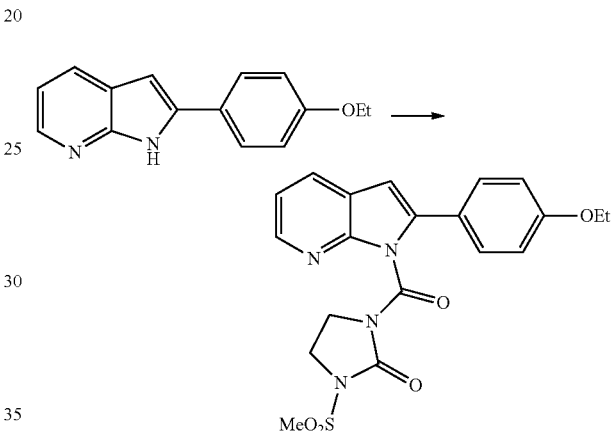

2-(4-ethoxyphenyl)-1H-pyrrolo[2,3-b]pyridine (100 mg, 0.42 mmol) was dissolved in anhydrous DMF (5 ml) under argon, treated with NaH (20 mg, 1.2 eq, 0.50 mmol) and stirred at r.t. for 15 min before adding (methylsulfonyl)-2-oxoimidazolidine-1-carbonyl chloride (209 mg, 2.2 eq, 0.92 mmol). The mixture was stirred 6 days at r.t., quenched with water and extracted with EtOAc (4×10 ml). The organic layer was washed with brine, dried over $MgSO_4$, filtered and concentrated. The crude product was purified by flash chromatography (50:50 PE:EtOAc) to afford an oil that was redissolved in $CH_2Cl_2$ and concentrated under hi-vacuum to obtain a white solid (41 mg, 23%).

$^1$H-NMR (300 MHz, $CDCl_3$): 1.44 (t, J=7.0 Hz, 3H), 3.17 (s, 3H), 3.88-3.94 (m, 4H), 4.07 (q, J=7.0 Hz, 2H), 6.60 (s, 1H), 6.95 (d, J=8.7 Hz, 2H), 7.17 (dd, J=7.8, 4.8 Hz, 1H), 7.41 (d, J=8.7 Hz, 2H), 7.88 (dd, J=7.8, 1.5 Hz, 1H), 8.23 (dd, J=4.8, 1.5 Hz, 1H).

Synthesis of 2-(4-ethoxyphenyl)-N,N-diisopropyl-7H-pyrrolo[2,3-b]pyridine-7-carboxamide (Compound 34)

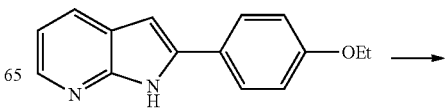

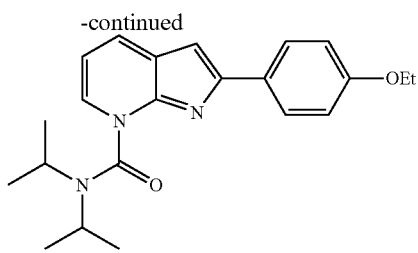

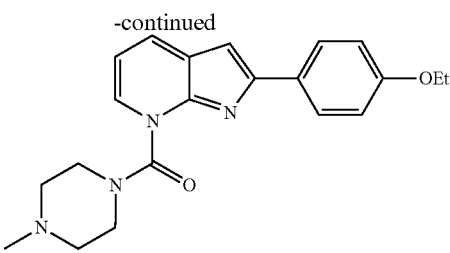

Following the same procedure as the synthesis of 2-(4-ethoxyphenyl)-N,N-diethyl-7H-pyrrolo[2,3-b]pyridine-7-carboxamide, using diisopropyl carbamoyl chloride, to obtain the desired product (8 mg, 5%).

$^1$H-NMR (300 MHz, CDCl$_3$): 1.08 (d, J=6.6 Hz, 3H), 1.29 (d, J=6.6 Hz, 3H), 1.43 (t, J=7.0 Hz, 3H), 1.63 (d, J=6.7 Hz, 3H), 1.77 (d, J=6.7 Hz, 3H), 3.25-3.39 (m, 1H), 3.66-3.78 (m, 1H), 4.08 (q, J=7.0 Hz, 2H), 6.81 (dd, J=7.3, 6.4 Hz, 1H), 6.89 (s, 1H), 6.93 (d, J=8.9 Hz, 2H), 7.51 (dd, J=6.4, 1.1 Hz, 1H), 7.93 (dd, J=7.3, 1.1 Hz, 1H), 8.06 (d, J=8.9 Hz, 2H).

Synthesis of (2-(4-ethoxyphenyl)-7H-pyrrolo[2,3-b]pyridin-7-yl)(pyrrolidin-1-yl)methanone (compound 35)

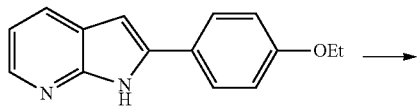

Following the same procedure as the synthesis of 2-(4-ethoxyphenyl)-N,N-diethyl-7H-pyrrolo[2,3-b]pyridine-7-carboxamide, using pyrrolidine-1-carbonyl chloride, to obtain the desired product (54 mg, 38%).

$^1$H-NMR (300 MHz, CDCl$_3$): 1.43 (t, J=7.0 Hz, 3H), 1.83-1.96 (m, 2H), 1.99-2.11 (m, 2H), 3.36-3.49 (m, 2H), 3.85-3.90 (m, 2H), 4.08 (q, J=7.0 Hz, 2H), 6.84 (dd, J=7.3, 6.5 Hz, 1H), 6.87 (s, 1H), 6.95 (d, J=8.9 Hz, 2H), 7.70 (dd, J=6.5, 1.1 Hz, 1H), 7.96 (dd, J=7.3, 1.0 Hz, 1H), 8.05 (d, J=8.9 Hz, 2H).

Synthesis of (2-(4-ethoxyphenyl)-7H-pyrrolo[2,3-b]pyridin-7-yl) (4-methylpiperazin-1-yl)methanone (Compound 36)

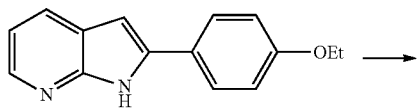

Following the same procedure as the synthesis of 2-(4-ethoxyphenyl)-N,N-diethyl-7H-pyrrolo[2,3-b]pyridine-7-carboxamide, using 4-methylpiperazine-1-carbonyl chloride, to obtain the desired product (7 mg, 2%).

$^1$H-NMR (300 MHz, CDCl$_3$): 1.42 (t, J=7.0 Hz, 3H), 2.37 (s, 3H), 2.55-2.87 (m, 4H), 3.06-3.13 (m, 2H), 3.38-3.45 (m, 1H), 3.89-4.01 (m, 1H), 4.09 (q, J=7.0 Hz, 2H), 6.84 (dd, J=7.5, 6.8 Hz, 1H), 6.88 (s, 1H), 6.94 (d, J=8.9 Hz, 2H), 7.64 (dd, J=6.8, 1.1 Hz, 2H), 7.96 (dd, J=7.5, 1.1 Hz, 1H), 8.06 (d, J=8.9 Hz, 2H).

II. Biological Tests of the Compounds According to the Invention

Example 2: Cell-based Screening of Chemical Libraries for Characterization of Necroptosis Inhibitors TNF-α can induce necroptosis in Jurkat cells (human T lymphocytes) when FADD was deleted. This model was used to screen various libraries of chemical compounds for characterization of new inhibitors of cellular necroptosis. Details on this cell-based assay can be found in Miao and Degterev (*Methods Mol. Biol.* 2009, 559, 79-93). The Jurkat FADD-deficient I 2.1 cell line used was purchased from ATCC and was maintained in RPMI 1640 medium (Gibco) containing Glutamax and 15% fetal calf serum (Life Technology). Necroptosis was induced by addition of 10 ng/ml of human recombinant TNF-α (Life Technology). Necrostatin-1 (Nec-1, Enzo Life Sciences) was used as model necroptosis inhibitor. Cells were maintained in 75 cm$^2$ flask and passed every 2 or 3 days. Chemical collections analysed were formatted in 96-well plates with 80 molecules per plates at 10 mM in 100% DMSO. For each collection plate, 2 cell plates were seeded (one necroptosis-induced with TNF-α and the other without TNF-α). Cells were seeded at 20000 cells/well, in 40 μl of medium, in a 96-well clear, flat bottom plate (CytoOne, Starlab) before treatment. Then, 40 μl of medium with or without TNF-α at 25 ng/ml were added to all wells in the corresponding plate. Immediately after TNF-α addition, 20 μl of diluted compound at 50 μM were added to the plates. Final concentration of each chemical compound was 10 μM at 0.1% DMSO. Four positives (Nec-1 at 10 μM final) and four negative (DMSO) controls were used in each plate to validate the assay. Cells were incubated at 37° C., 5% CO$_2$ for 24 hours before performing MTS viability assay, described hereafter. Compounds were diluted before to treat cells. Liquid handling was performed using the Nimbus Microlab liquid handler (Hamilton Robotics) under microbiological safety workbench. The 10 mM compounds were diluted at 50 μM directly in cell medium.

The results of these tests obtained with the compounds of the invention are indicated below and in FIGS. 1 to 11:

| N° | Compound | EC$_{50}$ (μM) | N° | Compound | EC$_{50}$ (μM) |
|---|---|---|---|---|---|
| 7 | | 7 | 10 | | 1.7 |
| 17 | | 3 | 26 | | 2.4 |
| 21 | | 5 | 32 | | 2.5 |
| 33 | | 1 | 34 | | 2 |
| 35 | | 3.5 | 36 | | 1.05 |

Besides, the EC$_{50}$ of compound 7, compound 10 and necrostatin-1 (Nec-1) were determined in mouse or human cellular models of necroptosis induced by FasL+zVAD-fmk (a pan-caspase inhibitor), TRAIL+zVAD-fmk+Bp (Birinapant, a Smac mimetics) or TNF, and by using two cytotoxic assays (MTS Cell Proliferation assay or intracellular ATP level). As shown in the table below, compound 10 inhibits TNF-, TRAIL- or FasL-induced necroptosis as Nec-1 whereas compound 7 only inhibits TNF- or FasL-induced necroptosis (Table 1).

TABLE 1 anti-necroptotic effect of compounds 7, 10, and Nec-1

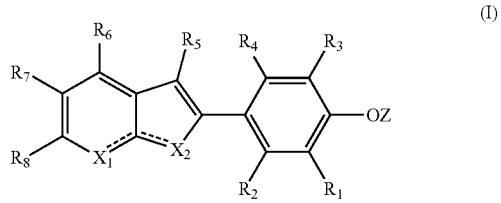

| Cell lines Necroptosis inducer | Assays | Compound 7 | Compound 10 | Nec-1 |
|---|---|---|---|---|
| L929sAhFas FasL + Zvad | ATP level | 5 µM | 5 µM | 10 µM |
|  | MTS | 10 µM | 3.5 µM | 10 µM |
| HT29 TRAIL + Zvad + Bp | ATP level | ND | 5 µM | 2 µM |
|  | MTS | ND | 4 µM | 1.2 µM |
| Jurkat Fadd$^{-/-}$ TNF | ATP level | 9.3 µM | 2.6 µM | 1.3 µM |
|  | MTS | 10 µM | 4 µM | 1.3 µM |

Example 3: RIPK1 Autophosphorylation Assay

RIPK1 Autophosphorylation Assay: Human RIPK1 full length GST-tagged was baculovirally expressed in Sf9 cells according to manufacturer's instructions (Bac-to-Bac expression system, Invitrogen) and purified using gluthation-sepharose beads (GE Healthcare). The elution was made in 50 mM Tris-HCl, pH 8.0 buffer supplemented with 30 mM reduced gluthatione (Sigma). The protocol used to detect the enzymatic activity is adapted from Miao and Degterev (*Methods Mol. Biol.* 2009, 559, 79-93). Kinase reaction was initiated mixing 5 µl of eluted RIPK1, 5 µl of 3× kinase reaction buffer (5 mM MOPS pH 7.2, 2.5 mM β-glycerophosphate, 4 mM MgCl$_2$, 2.5 mM MnCl$_2$, 1 mM EGTA, 0.4 mM EDTA, 50 µg/ml BSA, 0.05 mM DTT), 2 µl H$_2$O and 3 µl of the tested molecule. The mixture was kept on ice for 10 minutes. During the incubation, the ATP solution was prepared by mixing 5 µl of 3× kinase reaction buffer, 4 µl H$_2$O, 6 µl cold ATP at 150 µM and 2 µCi of [γ-$^{32}$P] ATP. Add the ATP solution and the tested inhibitor to the kinase and incubate for 30 minutes at 30° C. To stop the enzymatic reaction, 5 µl of loading buffer were added and solution was heated for 3 minutes at 95° C. 25 µl of each reaction were loaded per well in pre-cast NuPage 12% Bis-Tris gel (Life Technology). Autophosphorylated RIPK1 band was visualized on radiographic film after 6 h exposition at −80° C.

Figure 5:
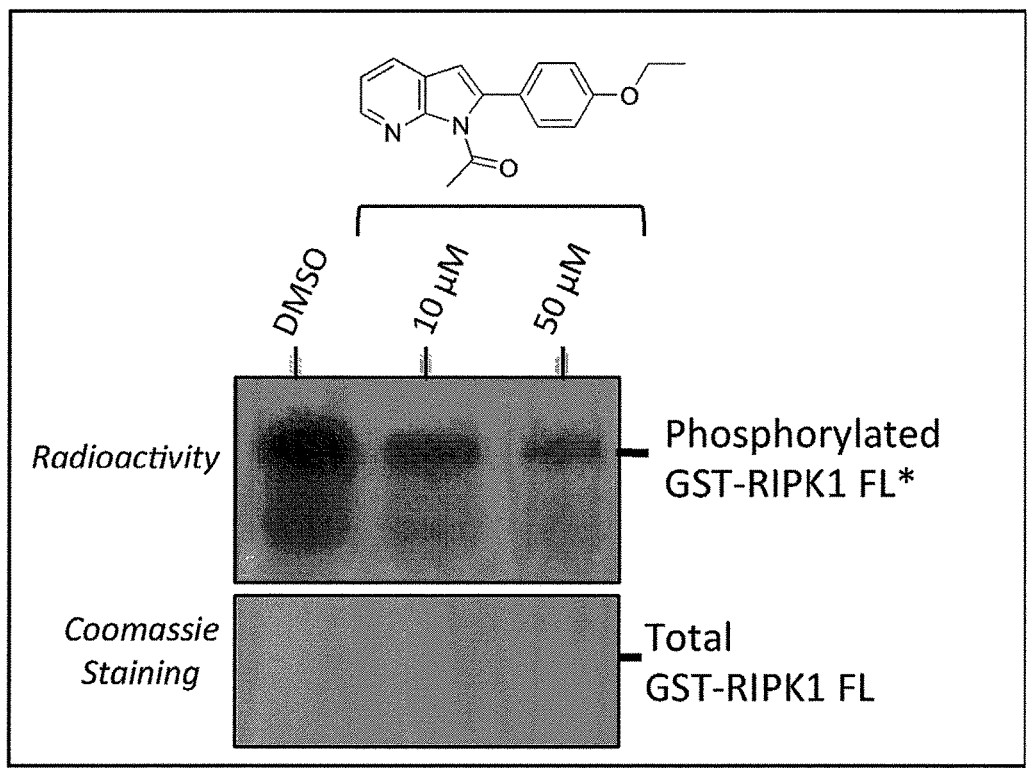
FIG. 5. represents the dose-dependent inhibition of RIPK1 autophosphorylation by compound 10.
Figures 6, 7:
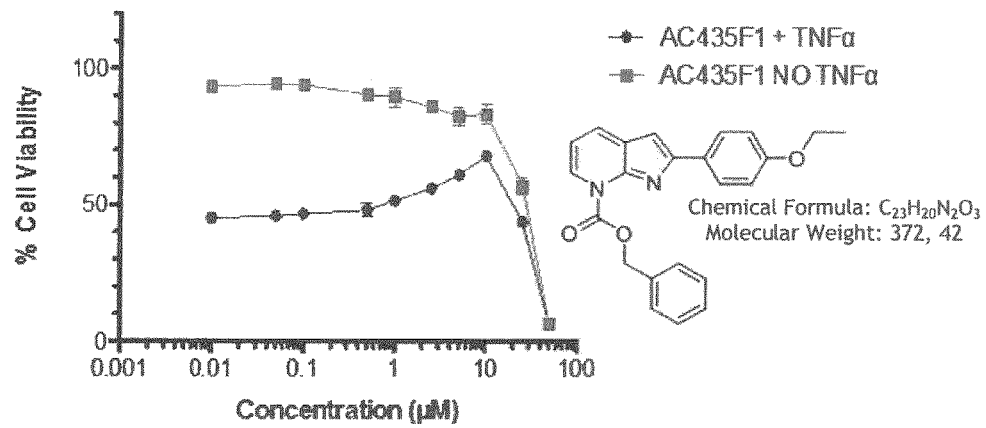
FIG. 6. represents the dose-dependent inhibition by compound 21 of necroptosis induced by TNF-α in human T lymphocyte (Jurkat FADD deficient cell line)
FIG. 7. represents the dose-dependent inhibition by compound 32 of necroptosis induced by TNF-α in human T lymphocyte (Jurkat FADD deficient cell line)
Figure 8:
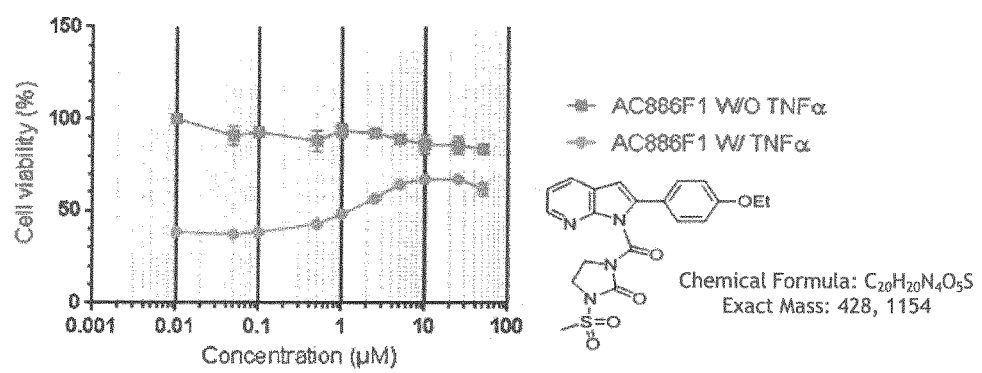
FIG. 8. represents the dose-dependent inhibition by compound 33 of necroptosis induced by TNF-α in human T lymphocyte (Jurkat FADD deficient cell line)
Figure 9:
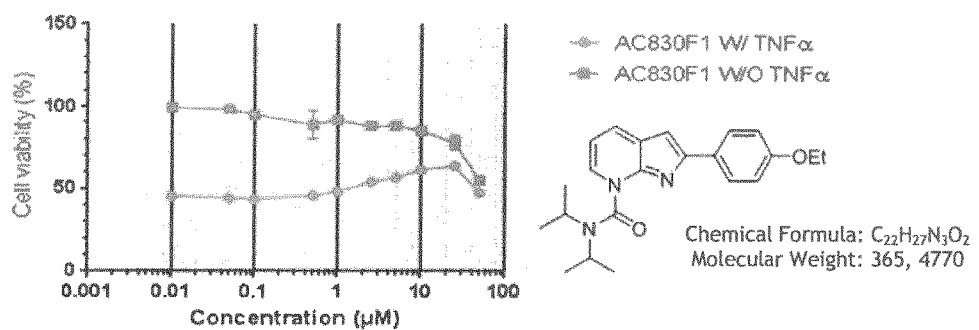
FIG. 9. represents the dose-dependent inhibition by compound 34 of necroptosis induced by TNF-α in human T lymphocyte (Jurkat FADD deficient cell line)
Figure 10:
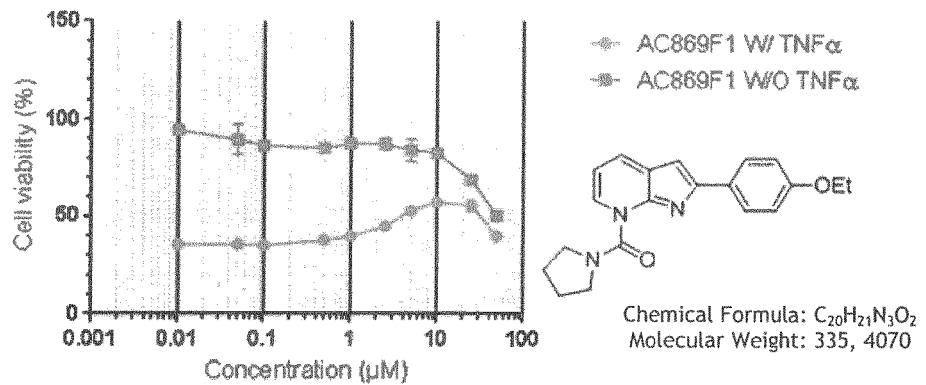
FIG. 10. represents the dose-dependent inhibition by compound 35 of necroptosis induced by TNF-α in human T lymphocyte (Jurkat FADD deficient cell line)
Figure 11:
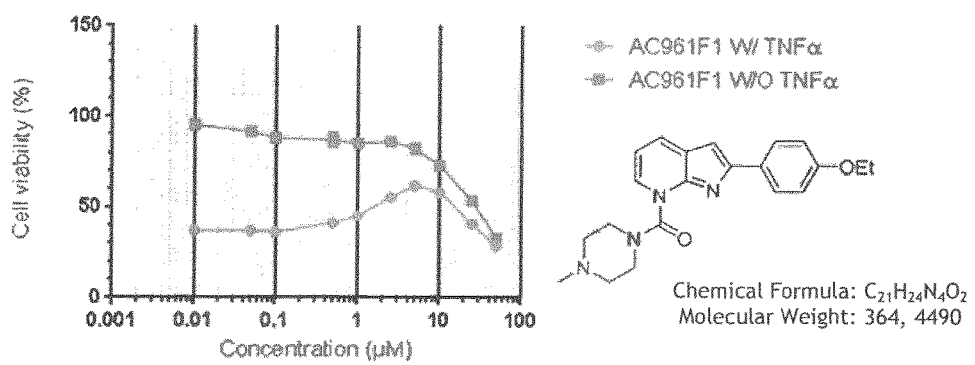
FIG. 11. represents the dose-dependent inhibition by compound 36 of necroptosis induced by TNF-α in human T lymphocyte (Jurkat FADD deficient cell line)

The results of this test obtained with compound 10 of the invention are indicated in FIG. 5. The decrease of the amount of radioactively labeled RIPK1 indicates that compound 10 (N1-Sibiriline derivative) inhibits, in a dose-dependent fashion, the RIPK1 autophosphorylation. As phosphorylation of RIPK1 requires its kinase activity, RIPK1 is thus a bona fide target of compound 10 to drive the inhibition of the necroptosis induced by TNF-α as shown in FIG. 5.

The invention claimed is:

1. A compound of formula (I):

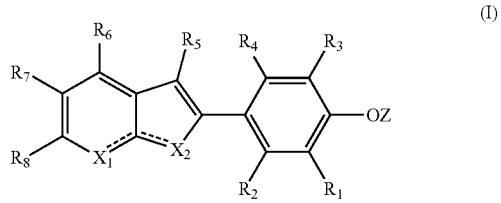

or a pharmaceutically acceptable salt thereof, wherein:

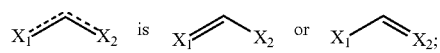

where (i) when

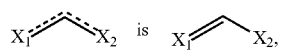

$X_1$ is N and $X_2$ is —N(Y)—, and (ii) when

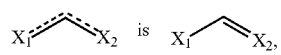

$X_1$ is —N(Y)— and $X_2$ is N;
$R_{alk}$ is —(C$_1$-C$_6$)alkyl;
$R_1$, $R_2$, $R_3$ and $R_4$ are independently —H, -halo, —(C$_1$-C$_6$)alkyl, —CF$_3$, —CN, —OR$_{51}$, —NR$_{52}$R$_{53}$ or —OS(O)$_2$NR$_{54}$R$_{55}$;
$R_5$ is —H, —(C$_1$-C$_6$)alkyl or —O(C$_1$-C$_6$)alkyl;
$R_6$, $R_7$ and $R_8$ are independently —H, -halo, —OR$_{56}$, —NR$_{57}$R$_{58}$, —C(O)NR$_{59}$R$_{60}$, —C(O)R$_{61}$, —R$_{62}$C(O)OR$_{63}$, —R$_{64}$C(O)R$_{65}$, —R$_{66}$NR$_{67}$R$_{68}$, —R$_{69}$OR$_{70}$, —S(O)$_2$R$_{74}$, —OR$_{75}$C(O)OR$_{76}$, —OC(O)R$_{77}$ or —C(O)OR$_{78}$; or $R_6$, $R_7$ and $R_8$ are independently —$(C_1$-$C_6)$alkyl, —$(C_1$-$C_6)$alkyl-aryl, —$(C_1$-$C_6)$alkyl-heterocycloalkyl, -heterocycloalkyl, -aryl or -heteroaryl, each optionally substituted with one or more substituents selected from the group consisting of -oxo, -halo, —$NO_2$, —CN, —$OR_{79}$, —$NR_{80}R_{81}$, —$SR_{82}$, —$S(O)R_{83}$, —$S(O)_2R_{84}$, —$S(O)_2NR_{85}R_{86}$, —$OC(O)R_{87}$, —$NR_{88}C(O)R_{89}$, —$NR_{90}C(O)OR_{91}$, —$C(O)OR_{92}$, —$C(O)NR_{93}R_{94}$, —$C(O)OR_{95}$, —$OC(O)NR_{96}R_{97}$ and —$C(O)R_{98}$;

$R_{10}$, $R_{11}$, $R_{12}$, $R_{25}$, $R_{29}$, $R_{51}$, $R_{52}$, $R_{53}$, $R_{54}$, $R_{55}$, $R_{56}$, $R_{57}$, $R_{58}$, $R_{59}$, $R_{60}$, $R_{61}$, $R_{62}$, $R_{63}$, $R_{64}$, $R_{65}$, $R_{66}$, $R_{67}$, $R_{68}$, $R_{69}$, $R_{70}$, $R_{74}$, $R_{75}$, $R_{76}$, $R_{77}$, $R_{78}$, $R_{79}$, $R_{80}$, $R_{81}$, $R_{82}$, $R_{83}$, $R_{84}$, $R_{85}$, $R_{86}$, $R_{87}$, $R_{88}$, $R_{89}$, $R_{90}$, $R_{91}$, $R_{92}$, $R_{93}$, $R_{94}$, $R_{95}$, $R_{96}$, $R_{97}$ and $R_{98}$ are independently —H or -halo; or $R_{10}$, $R_{11}$, $R_{12}$, $R_{25}$, $R_{29}$, $R_{51}$, $R_{52}$, $R_{53}$, $R_{54}$, $R_{55}$, $R_{56}$, $R_{57}$, $R_{58}$, $R_{59}$, $R_{60}$, $R_{61}$, $R_{62}$, $R_{63}$, $R_{64}$, $R_{65}$, $R_{66}$, $R_{67}$, $R_{68}$, $R_{69}$, $R_{70}$, $R_{74}$, $R_{75}$, $R_{76}$, $R_{77}$, $R_{78}$, $R_{79}$, $R_{80}$, $R_{81}$, $R_{82}$, $R_{83}$, $R_{84}$, $R_{85}$, $R_{86}$, $R_{87}$, $R_{88}$, $R_{89}$, $R_{90}$, $R_{91}$, $R_{92}$, $R_{93}$, $R_{94}$, $R_{95}$, $R_{96}$, $R_{97}$ and $R_{98}$ are independently —$(C_1$-$C_6)$alkyl, —$(C_1$-$C_6)$alkyl-aryl, -heterocycloalkyl, -aryl or -heteroaryl, each optionally substituted with one or more substituents selected from the group consisting of -oxo, -halo, —$(C_1$-$C_6)$alkyl, —$OR_{alk}$, —$S(O)_2R_{alk}$, —$C(O)OR_{alk}$ and —$C(O)R_{alk}$; or $R_{57}$ and $R_{58}$, together with the nitrogen atom to which they are attached, form a heterocycloalkyl group; and/or $R_{59}$ and $R_{60}$, together with the nitrogen atom to which they are attached, form a heterocycloalkyl group; and/or $R_{67}$ and $R_{68}$, together with the nitrogen atom to which they are attached, form a heterocycloalkyl group; and/or $R_{80}$ and $R_{81}$, together with the nitrogen atom to which they are attached, form a heterocycloalkyl group; and/or $R_{85}$ and $R_{86}$, together with the nitrogen atom to which they are attached, form a heterocycloalkyl group; and/or $R_{93}$ and $R_{94}$, together with the nitrogen atom to which they are attached, form a heterocycloalkyl group; and/or $R_{96}$ and $R_{97}$, together with the nitrogen atom to which they are attached, form a heterocycloalkyl group;

Y is —$C(O)NR_{10}R_{11}$, —$C(O)R_{12}$, —$S(O)_2R_{25}$ or —$C(O)OR_{29}$; and Z is —$CH_2CH_3$.

2. The compound according to claim 1, or a pharmaceutically acceptable salt thereof, wherein $R_1$, $R_2$, $R_3$ and $R_4$ are independently —H, -halo, —$(C_1$-$C_6)$alkyl or —$OR_{51}$.

3. The compound according to claim 2, or a pharmaceutically acceptable salt thereof, wherein $R_1$, $R_2$, $R_3$ and $R_4$ are independently —H, -halo, —$CH_3$ or —$OCH_3$.

4. The compound according to claim 1, or a pharmaceutically acceptable salt thereof, wherein $R_5$ is —H.

5. The compound according to claim 1, or a pharmaceutically acceptable salt thereof, wherein:

$R_6$, $R_7$ and $R_8$ are independently —H, -halo, —$OR_{56}$ or —$NR_{57}R_{58}$; or $R_6$, $R_7$ and $R_8$ are independently —$(C_1$-$C_6)$alkyl, —$(C_1$-$C_6)$alkyl-aryl, —$(C_1$-$C_6)$alkyl-heterocycloalkyl, -heterocycloalkyl, -aryl or -heteroaryl, each optionally substituted with one or more substituents selected from the group consisting of -oxo, -halo, —$NO_2$, —CN, —$OR_{79}$, —$NR_{80}R_{81}$, —$SR_{82}$, —$S(O)R_{83}$, —$S(O)_2R_{84}$, —$S(O)_2NR_{85}R_{86}$, —$OC(O)R_{87}$, —$NR_{88}C(O)R_{89}$, —$NR_{90}C(O)OR_{91}$, —$C(O)OR_{92}$, —$C(O)NR_{93}R_{94}$, —$C(O)OR_{95}$, —$OC(O)NR_{96}R_{97}$ and —$C(O)R_{98}$.

6. The compound according to claim 5, or a pharmaceutically acceptable salt thereof, wherein:

$R_6$, $R_7$ and $R_8$ are independently —H, -halo, —$OR_{56}$ or —$NR_{57}R_{58}$; or $R_6$, $R_7$ and $R_8$ are independently —$(C_1$-$C_6)$alkyl, -heterocycloalkyl, -aryl or -heteroaryl.

7. The compound according to claim 1, or a pharmaceutically acceptable salt thereof, wherein:

$R_{10}$, $R_{11}$, $R_{12}$, $R_{25}$, $R_{29}$, $R_{51}$, $R_{52}$, $R_{53}$, $R_{54}$, $R_{55}$, $R_{56}$, $R_{57}$, $R_{58}$, $R_{59}$, $R_{60}$, $R_{61}$, $R_{62}$, $R_{63}$, $R_{64}$, $R_{65}$, $R_{66}$, $R_{67}$, $R_{68}$, $R_{69}$, $R_{70}$, $R_{74}$, $R_{75}$, $R_{76}$, $R_{77}$, $R_{78}$, $R_{79}$, $R_{80}$, $R_{81}$, $R_{82}$, $R_{83}$, $R_{84}$, $R_{85}$, $R_{86}$, $R_{87}$, $R_{88}$, $R_{89}$, $R_{90}$, $R_{91}$, $R_{92}$, $R_{93}$, $R_{94}$, $R_{95}$, $R_{96}$, $R_{97}$ and $R_{98}$ are independently —H or -halo; or $R_{10}$, $R_{11}$, $R_{12}$, $R_{25}$, $R_{29}$, $R_{51}$, $R_{52}$, $R_{53}$, $R_{54}$, $R_{55}$, $R_{56}$, $R_{57}$, $R_{58}$, $R_{59}$, $R_{60}$, $R_{61}$, $R_{62}$, $R_{63}$, $R_{64}$, $R_{65}$, $R_{66}$, $R_{67}$, $R_{68}$, $R_{69}$, $R_{70}$, $R_{74}$, $R_{75}$, $R_{76}$, $R_{77}$, $R_{78}$, $R_{79}$, $R_{80}$, $R_{81}$, $R_{82}$, $R_{83}$, $R_{84}$, $R_{85}$, $R_{86}$, $R_{87}$, $R_{88}$, $R_{89}$, $R_{90}$, $R_{91}$, $R_{92}$, $R_{93}$, $R_{94}$, $R_{95}$, $R_{96}$, $R_{97}$ and $R_{98}$ are independently —$(C_1$-$C_6)$alkyl, benzyl, -heterocycloalkyl or phenyl, each optionally substituted with one or more substituents selected from the group consisting of -oxo, -halo, —$(C_1$-$C_6)$alkyl, —$OR_{alk}$, —$S(O)_2R_{alk}$, —$C(O)OR_{alk}$ and —$C(O)R_{alk}$.

8. The compound according to claim 7, or a pharmaceutically acceptable salt thereof, wherein:

$R_{10}$, $R_{11}$, $R_{12}$, $R_{25}$, $R_{29}$, $R_{51}$, $R_{52}$, $R_{53}$, $R_{54}$, $R_{55}$, $R_{56}$, $R_{57}$, $R_{58}$, $R_{59}$, $R_{60}$, $R_{61}$, $R_{62}$, $R_{63}$, $R_{64}$, $R_{65}$, $R_{66}$, $R_{67}$, $R_{68}$, $R_{69}$, $R_{70}$, $R_{74}$, $R_{75}$, $R_{76}$, $R_{77}$, $R_{78}$, $R_{79}$, $R_{80}$, $R_{81}$, $R_{82}$, $R_{83}$, $R_{84}$, $R_{85}$, $R_{86}$, $R_{87}$, $R_{88}$, $R_{89}$, $R_{90}$, $R_{91}$, $R_{92}$, $R_{93}$, $R_{94}$, $R_{95}$, $R_{96}$, $R_{97}$ and $R_{98}$ are independently —H or -halo; or $R_{10}$, $R_{11}$, $R_{12}$, $R_{25}$, $R_{29}$, $R_{51}$, $R_{52}$, $R_{53}$, $R_{54}$, $R_{55}$, $R_{56}$, $R_{57}$, $R_{58}$, $R_{59}$, $R_{60}$, $R_{61}$, $R_{62}$, $R_{63}$, $R_{64}$, $R_{65}$, $R_{66}$, $R_{67}$, $R_{68}$, $R_{69}$, $R_{70}$, $R_{74}$, $R_{75}$, $R_{76}$, $R_{77}$, $R_{78}$, $R_{79}$, $R_{80}$, $R_{81}$, $R_{82}$, $R_{83}$, $R_{84}$, $R_{85}$, $R_{86}$, $R_{87}$, $R_{88}$, $R_{89}$, $R_{90}$, $R_{91}$, $R_{92}$, $R_{93}$, $R_{94}$, $R_{95}$, $R_{96}$, $R_{97}$ and $R_{98}$ are independently —$(C_1$-$C_6)$alkyl, benzyl, -heterocycloalkyl or phenyl, each optionally substituted with one or more substituents selected from the group consisting of -oxo, -halo, —$CH_3$ and —$S(O)_2CH_3$.

9. The compound according to claim 1, wherein the compound is selected from the group consisting of:

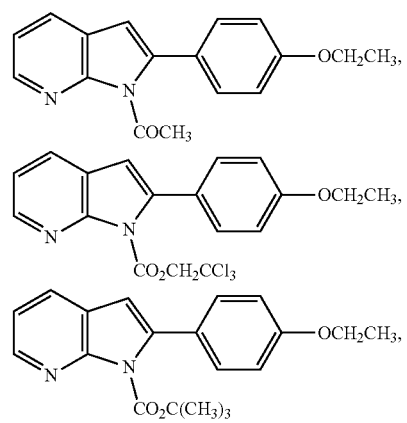

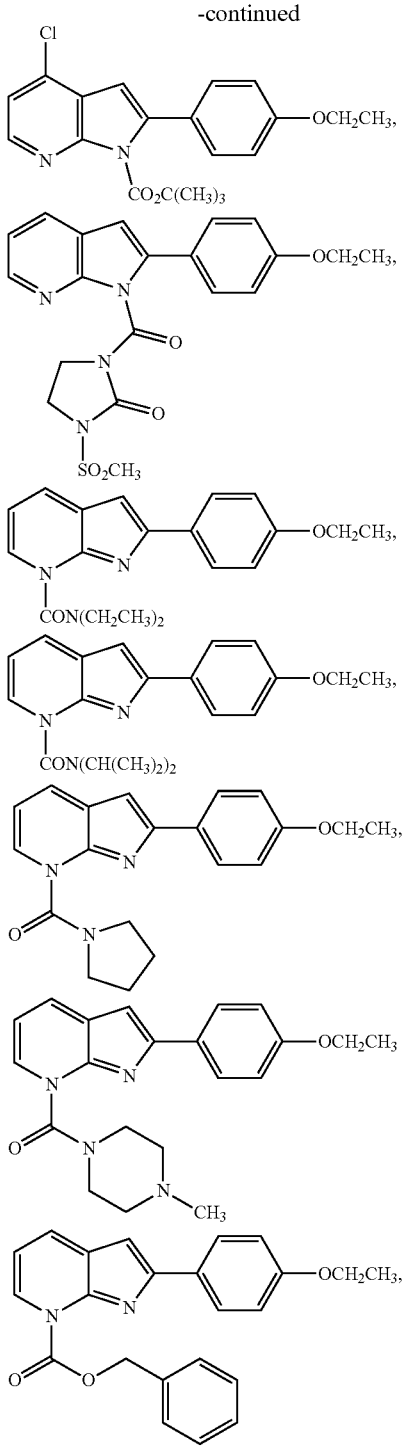

or a pharmaceutically acceptable salt thereof.

10. A pharmaceutical composition comprising at least one compound according to claim 1, or a pharmaceutically acceptable salt thereof, and at least one pharmaceutically acceptable excipient.

11. A method for inhibiting cellular necroptosis in a patient, comprising administering to the patient in need thereof a therapeutically effective amount of a compound according to claim 1, or a pharmaceutically acceptable salt thereof.

12. The method according to claim 11, wherein the cellular necroptosis is tumor-cell-induced endothelial cell necroptosis.

13. The method according to claim 12, wherein the tumor-cell-induced endothelial cell necroptosis is selected from the group consisting of tumor cell extravasation and tumor cell metastasis.

14. The method according to claim 11, wherein the patient has a disorder associated with cellular necroptosis selected from the group consisting of a trauma in the brain, a viral infection, acute pancreatitis, acute tubular necrosis, alcoholic steatohepatitis, atherosclerosis, bone marrow failure, chronic obstructive pulmonary disease, Crohn's colitis, heart transplantation, hepatitis, ischemia reperfusion injury, kidney transplantation, non-alcoholic steatohepatitis, terminal ileitis and ulcerative colitis.

15. The method according to claim 14, wherein the ischemia reperfusion injury is selected from the group consisting of a myocardial infarction and a stroke.

16. A method for preserving and/or protecting a biological material, comprising placing the biological material in a medium comprising a compound according to claim 1, or a pharmaceutically acceptable salt thereof.

17. The method according to claim 16, wherein the biological material is a cell, a tissue, a body fluid, an organ or a microorganism.

18. A process for preparing a compound of formula (I) according to claim 1:

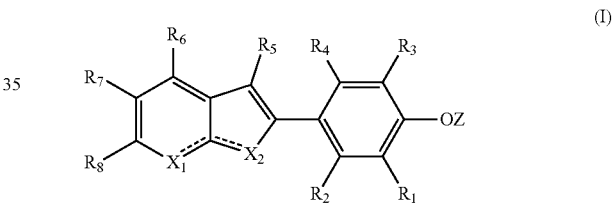

or a pharmaceutically acceptable salt thereof,
wherein:

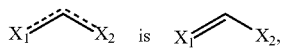

$X_1$ is N and $X_2$ is —N(Y)—;

$R_{alk}$ is —($C_1$-$C_6$)alkyl;

$R_1$, $R_2$, $R_3$ and $R_4$ are independently —H;

$R_5$ is —H;

$R_6$, $R_7$ and $R_8$ are independently —H;

$R_{10}$, $R_{11}$, $R_{12}$, $R_{25}$ and $R_{29}$ are independently —H or -halo; or $R_{10}$, $R_{11}$, $R_{12}$, $R_{25}$ and $R_{29}$ are independently —($C_1$-$C_6$) alkyl, —($C_1$-$C_6$)alkyl-aryl, -heterocycloalkyl, -aryl or -heteroaryl, each optionally substituted with one or more substituents selected from the group consisting of -oxo, -halo, —($C_1$-$C_6$)alkyl, —$OR_{alk}$, —$S(O)_2R_{alk}$, —$C(O)OR_{alk}$ and —$C(O)R_{alk}$; or Y is —$C(O)NR_{10}R_{11}$, —$C(O)R_{12}$, —$S(O)_2R_{25}$ or —$C(O)OR_{29}$; and Z is —$CH_2C_3$;

wherein the process comprises the following steps:
1) reacting a compound of the formula:

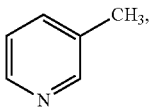

with a compound of the formula:

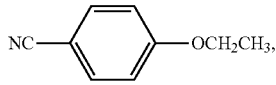

in the presence of a solvent selected from the group consisting of dichloromethane, N,N-dimethylformamide, dimethylsulfoxide, N-methylpyrrolidone, tetrahydrofuran, acetic anhydride and anhydrous toluene, or a combination thereof, and a base selected from the group consisting of triethylamine, diisopropylethylamine, 1,4-diazabicyclo[2.2.2]octane, sodium hydride, lithium diisopropylamide, lithium hexamethyldisilazane, n-butyllithium, isopropylmagnesium chloride, potassium tert-butoxide, potassium carbonate, potassium hydroxide, sodium hydroxide, cesium carbonate and potassium phosphate, to provide a compound of formula (II):

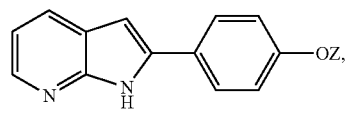

(II)

wherein:
Z is —CH$_2$CH$_3$;
2) reacting the compound of formula (II) above with a compound of the formula:

Y—W, wherein:
Y is —C(O)NR$_{10}$R$_{11}$, —C(O)R$_{12}$, —S(O)$_2$R$_{25}$ or —C(O)OR$_{29}$;
W is halo; and
R$_{10}$, R$_{11}$, R$_{12}$, R$_{25}$ and R$_{29}$ are independently —H or -halo; or
R$_{10}$, R$_{11}$, R$_{12}$, R$_{25}$ and R$_{29}$ are independently —(C$_1$-C$_6$)alkyl, —(C$_1$-C$_6$)alkyl-aryl, -heterocycloalkyl, -aryl or -heteroaryl, each optionally substituted with one or more substituents selected from the group consisting of -oxo, -halo, —(C$_1$-C$_6$)alkyl, —S(O)$_2$R$_{alk}$, —C(O)OR$_{alk}$ and —C(O)R$_{alk}$;
in the presence of a base selected from the group consisting of triethylamine, diisopropylethylamine, 1,4-diazabicyclo[2.2.2]octane, sodium hydride, lithium diisopropylamide, lithium hexamethyldisilazane, isopropylmagnesium chloride, potassium tert-butoxide, potassium carbonate, potassium hydroxide, sodium hydroxide, cesium carbonate and potassium phosphate and optionally a catalyst selected from the group consisting of copper iodide, tetrabutylammonium iodide, N,N-dimethylamopyridine and N,N'-dimethylethylenediamine, to provide the compound of formula (I) above according to claim 1; and
3) optionally reacting the compound of formula (I) above according to claim 1 with an acid or base in the presence of a solvent selected from the group consisting of dichloromethane, N,N-dimethylformamide, dimethylsulfoxide, N-methylpyrrolidone, tetrahydrofuran, acetic anhydride and anhydrous toluene, or a combination thereof, to provide a pharmaceutically acceptable salt thereof.

19. A process for preparing a compound of formula (I) according to claim 1:

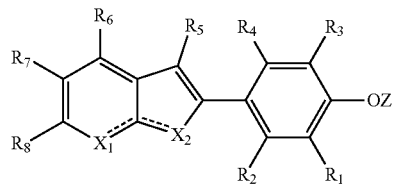

(I)

or a pharmaceutically acceptable salt thereof,
wherein:

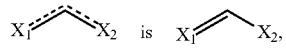

$X_1$ is N and $X_2$ is —N(Y)—;
$R_{alk}$ is —(C$_1$-C$_6$)alkyl;
$R_1$, $R_2$, $R_3$ and $R_4$ are independently —H;
$R_5$ is —H;
$R_6$, $R_7$ and $R_8$ are independently —H;
$R_{10}$, $R_{11}$, $R_{12}$, $R_{25}$ and $R_{29}$ are independently —H or -halo; or
$R_{10}$, $R_{11}$, $R_{12}$, $R_{25}$ and $R_{29}$ are independently —(C$_1$-C$_6$)alkyl, —(C$_1$-C$_6$)alkyl-aryl, -heterocycloalkyl, -aryl or -heteroaryl, each optionally substituted with one or more substituents selected from the group consisting of -oxo, -halo, —(C$_1$-C$_6$)alkyl, —OR$_{alk}$, —S(O)$_2$R$_{alk}$, —C(O)OR$_{alk}$ and —C(O)R$_{alk}$; or
Y is —C(O)NR$_{10}$R$_{11}$, —C(O)R$_{12}$, —S(O)$_2$R$_{25}$ or —C(O)OR$_{29}$; and
Z is —CH$_2$CH$_3$;
wherein the process comprises the following steps:
1) reacting a compound of the formula:

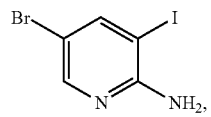

with a compound of the formula:

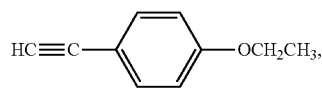

in the presence of a solvent selected from the group consisting of tetrahydrofuran, dioxane and triethylamine and a catalyst selected from the group consisting of PdCl$_2$(PPh$_3$)$_2$ and copper iodide, to provide a compound of formula (III):

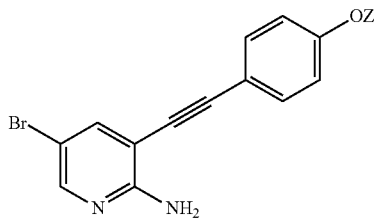

(III)

wherein:
Z is —CH$_2$CH$_3$;

2) reacting the compound of formula (III) above with a compound of the formula:

Y—W, wherein:
Y is —C(O)NR$_{10}$R$_{11}$, —C(O)R$_{12}$, —S(O)$_2$R$_{25}$ or —C(O)OR$_{29}$;
W is halo; and
R$_{10}$, R$_{11}$, R$_{12}$, R$_{25}$ and R$_{29}$ are independently —H or -halo; or
R$_{10}$, R$_{11}$, R$_{12}$, R$_{25}$ and R$_{29}$ are independently —(C$_1$-C$_6$)alkyl, —(C$_1$-C$_6$)alkyl-aryl, -heterocycloalkyl, -aryl or -heteroaryl, each optionally substituted with one or more substituents selected from the group consisting of -oxo, -halo, —(C$_1$-C$_6$)alkyl, —OR$_{alk}$, —S(O)$_2$R$_{alk}$, —C(O)OR$_{alk}$ and —C(O)R$_{alk}$;

in the presence of a solvent selected from the group consisting of dichloromethane, N,N-dimethylformamide, dimethylsulfoxide, N-methylpyrrolidone, tetrahydrofuran, acetic anhydride and anhydrous toluene, or a combination thereof, and a base selected from the group consisting of triethylamine, pyridine, diisopropylethylamine, 1,4-diazabicyclo[2.2.2]octane, sodium hydride, lithium diisopropylamide, lithium hexamethyldisilazane, n-butyllithium, isopropylmagnesium chloride, potassium tert-butoxide, potassium carbonate, potassium hydroxide, sodium hydroxide, cesium carbonate and potassium phosphate, to provide a compound of formula (IV):

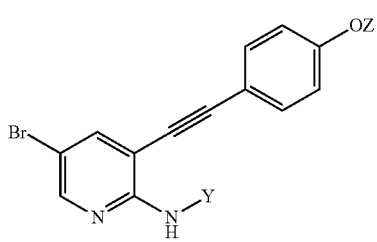

(IV)

wherein:
Y is —C(O)NR$_{10}$R$_{11}$, —C(O)R$_{12}$, —S(O)$_2$R$_{25}$ or —C(O)OR$_{29}$; and
Z is —CH$_2$CH$_3$; and 3) dissolving the compound of formula (IV) above in anhydrous N,N-dimethylformamide;

4) reacting the solution formed in step 3) above with cuprous iodide, to provide the compound of formula (I) above according to claim 1; and 5) optionally reacting the compound of formula (I) above according to claim 1 with an acid or base in the presence of a solvent selected from the group consisting of dichloromethane, N,N-dimethylformamide, dimethylsulfoxide, N-methylpyrrolidone, tetrahydrofuran, acetic anhydride and anhydrous toluene, or a combination thereof, to provide a pharmaceutically acceptable salt thereof.

* * * * *